(12) United States Patent
Akhavan-Tafti et al.

(10) Patent No.: US 10,241,111 B2
(45) Date of Patent: Mar. 26, 2019

(54) ELECTROLUMINESCENT BINDING ASSAYS

(71) Applicant: AhuraTech LLC, Brighton, MI (US)

(72) Inventors: Hashem Akhavan-Tafti, Howell, MI (US); Ali Ghiaseddin, Howell, MI (US)

(73) Assignee: AhuraTech LLC, Brighton, MI (US)

(*) Notice: Subject to any disclaimer, the term of this patent is extended or adjusted under 35 U.S.C. 154(b) by 0 days.

(21) Appl. No.: 16/119,036

(22) Filed: Aug. 31, 2018

(65) Prior Publication Data

US 2019/0011439 A1 Jan. 10, 2019

Related U.S. Application Data

(63) Continuation-in-part of application No. 16/005,085, filed on Jun. 11, 2018, which is a continuation-in-part of application No. 15/681,996, filed on Aug. 21, 2017, now Pat. No. 10,021,761, which is a continuation-in-part of application No. 15/331,027, filed on Oct. 21, 2016, now Pat. No. 9,756,701.

(51) Int. Cl.
*G01N 33/543* (2006.01)
*H05B 33/14* (2006.01)
*H05B 33/26* (2006.01)

(52) U.S. Cl.
CPC ... *G01N 33/5438* (2013.01); *G01N 33/54306* (2013.01); *G01N 33/54346* (2013.01); *H05B 33/14* (2013.01); *H05B 33/26* (2013.01)

(58) Field of Classification Search
CPC ..... H05B 33/14; H05B 33/26; G01N 33/5438
See application file for complete search history.

(56) References Cited

U.S. PATENT DOCUMENTS

| 2,901,651 | A | 8/1959 | Destriau |
| 5,220,243 | A | 6/1993 | Klinedinst et al. |
| 5,308,754 | A | 5/1994 | Kankare et al. |
| 5,893,999 | A | 4/1999 | Tamatani et al. |
| 6,054,809 | A | 4/2000 | Haynes et al. |
| 6,136,268 | A | 10/2000 | Ala-Kleme et al. |

(Continued)

FOREIGN PATENT DOCUMENTS

| EP | 1204858 B1 | 5/2008 |
| EP | 1495315 B1 | 8/2013 |

(Continued)

OTHER PUBLICATIONS

G. Destriau et al "Electroluminescence and Related Topics", IRE, Aug. 5, 1955.

(Continued)

*Primary Examiner* — Douglas W Owens
*Assistant Examiner* — Pedro C Fernandez
(74) *Attorney, Agent, or Firm* — Harness, Dickey & Pierce, P.L.C.

(57) ABSTRACT

Methods of producing light in liquid media are provided using nanoparticles capable of generating electroluminescence when stimulated by an electrical signal. The nanoparticles are provided as a label on a target species or on a specific binding partner of the target species to be detected in a test method. The nanoparticle-labeled species are drawn into operable proximity to electrodes which, when energized by a power source, excite the nanoparticles to produce electroluminescence. Methods of performing binding assays are described using the disclosed methods.

52 Claims, 17 Drawing Sheets

(56) References Cited

U.S. PATENT DOCUMENTS

| | | |
|---|---|---|
| 6,251,690 B1 | 6/2001 | Kulmala et al. |
| 6,274,323 B1 | 8/2001 | Bruchez et al. |
| 6,288,221 B1 | 9/2001 | Grinstaff et al. |
| 6,630,307 B2 | 10/2003 | Bruchez et al. |
| 6,645,776 B2 | 11/2003 | Kulmala et al. |
| 6,821,730 B2 | 11/2004 | Hannah |
| 7,005,108 B2 | 2/2006 | Ala-Kleme et al. |
| 7,513,983 B2 | 4/2009 | Ala-Kleme et al. |
| 7,700,366 B2 | 4/2010 | Swager et al. |
| 7,897,786 B2 | 3/2011 | Ulrich et al. |
| 8,304,259 B2 | 11/2012 | Isobe |
| 8,394,259 B2 | 3/2013 | Palmas et al. |
| 9,756,701 B1 | 9/2017 | Akhavan-Tafti et al. |
| 2002/0084454 A1 | 7/2002 | Kim et al. |
| 2002/0177695 A1 | 11/2002 | Grinstaff et al. |
| 2005/0019955 A1 | 1/2005 | Dahl et al. |
| 2005/0276993 A1 | 12/2005 | Sohn et al. |
| 2007/0170418 A1 | 7/2007 | Bowers et al. |
| 2007/0194694 A1 | 8/2007 | Reddy |
| 2008/0102534 A1 | 5/2008 | Ulrich et al. |
| 2009/0167145 A1 | 7/2009 | Withnall et al. |
| 2009/0278141 A1* | 11/2009 | Coe-Sullivan ......... B82Y 20/00 257/89 |
| 2011/0108738 A1 | 5/2011 | Doty et al. |
| 2012/0119639 A1 | 5/2012 | Staats et al. |
| 2013/0038202 A1 | 2/2013 | Donners |
| 2014/0234999 A1* | 8/2014 | Kim ...................... C09K 11/02 438/26 |
| 2015/0251152 A1 | 9/2015 | Buchholz et al. |
| 2016/0230088 A1* | 8/2016 | Puetz .................... C09K 11/02 |
| 2016/0336526 A1* | 11/2016 | Hirosawa ............... B82Y 20/00 |
| 2018/0202903 A1 | 7/2018 | Chou et al. |

FOREIGN PATENT DOCUMENTS

| | | |
|---|---|---|
| JP | 2010237020 A | 10/2010 |
| KR | 101560846 B1 | 10/2015 |
| WO | WO-2005073338 A2 | 8/2005 |
| WO | WO-2007013601 A1 | 2/2007 |
| WO | WO-2010058328 A2 | 5/2010 |

OTHER PUBLICATIONS

Mingyuan Gao et al "Photoluminescence and Electroluminescence of CdSe and CdTe Nanoparticles", 9th Climtec-World Forum on New Materials, Symposium X, (1999).

Vivek Makeshwari et al "Mineralization of Monodispersed CdS Nanoparticles on Polyelectrolyte Superstructure Forming an Electroluminescent Necklace-of-Beads", Langmuir 22, pp. 8623-8626 (2006).

S. Yamamoto "Evaluation of Distributed Inorganic Electroluminescence (EL) Devices With Comb Electrodes" Trans Mat. Res. Soc. Japan (2013).

L. N. Tripathi et al "Dielectric Dependence of EL Brightness of Powdered Phosphor and Particle Size Distribution" Phy. Stat. Sol. (a) 64, 297 (1981).

J. Kim "High Electroluminescence of the ZnS:Mn nanoparticle/cyanoethyl-resin polymer/single-walled carbon nanoube composite using the tandem structure" Journal of Materials Chemistry, vol. 22, (2012).

W. Lehmann "Contact Electroluminescence", Journal of the Electrochemical Society, vol. 104, No. 1 (1957).

International Search Report and Written Opinion dated Dec. 9, 2016, regarding PCT/US2016/049633.

International Search Report and Written Opinion dated Dec. 11, 2017 regarding PCT/US2017/049606.

* cited by examiner

Control
(BSA)

Sample
(btBSA)

Control      Sample

Control　　　　Sample

ELECTROLUMINESCENT BINDING ASSAYS

CROSS-REFERENCE TO RELATED APPLICATIONS

This application is a continuation-in-part of U.S. patent application Ser. No. 16/005,085 filed on Jun. 11, 2018 which is a continuation-in-part of U.S. patent application Ser. No. 15/681,996 filed on Aug. 21, 2017 (now U.S. Pat. No. 10,021,761) which is a continuation-in-part of U.S. patent application Ser. No. 15/331,027 filed on Oct. 21, 2016 (now U.S. Pat. No. 9,756,701). The entire disclosures of each of the above applications are incorporated herein by reference.

FIELD

The present disclosure relates to test methods for detecting and measuring the presence or amount of a target species in a sample by exciting electroluminescent material in a liquid medium.

BACKGROUND

Electroluminescence (EL) is the emission of light from a material in response to an electric stimulus. In a typical construct, a light emitting device is formed by providing an electroluminescent material between two electrodes. The electroluminescent material and the corresponding light emitting device are operated in dry or non-polar liquid media conditions, not in polar liquid media. The use of luminescent materials in polar liquid media has been limited only to photoluminescence, where the luminescent particles absorb higher energy light from an external light source and re-emit the absorbed energy as longer wavelength and lower energy light. A major drawback with such applications is that the high-intensity excitation light source can produce a substantial background which overwhelms the secondary light emitted by the luminescent material. Optical filters may be used to block the excitation light from entering a light detector, however they do not fully eliminate the background. The use of optical filters is especially problematic in cases where the re-emitted light from the luminescent materials is already very weak, or there is significant overlap between the excitation and emission wavelengths.

Applicants have recently discovered that significant luminescence emission can be elicited from particulate semiconductor materials in liquid media, including aqueous media (See, U.S. Pat. No. 9,756,701B2 and U.S. Ser. No. 10/021,761B2). Electrical excitation of these materials at a pair of electrodes with a time-varying electric current generates intense visible electroluminescence.

Various highly sensitive assays have been described which make use of the specific binding properties of certain molecules to detect the presence of an analyte or target species of interest in a sample. One category of such assays typically involves the specific binding between immunoglobulins such as antibodies or antibody fragments and haptens or antigens to which the immunoglobulins bind. Examples of such assays include enzyme-linked immunosorbent assays (ELISAs) and radio-immunoassay (RIA). Another category of specific binding assays that has received much attention involves the hybridization of nucleic acid strands having complementary base sequences.

In order to detect such binding or hybridization between the analyte of interest and a cognate partner having a specific affinity therefor, it is typically necessary for the partner of be labeled with a detectable label. Known labels include enzymes, radio-labels, fluorescent or chemiluminescent labels, mass tags, electrochemically active labels (such as redox labels) which undergo further chemical reaction with additional reaction components, and colored particles, e.g. latex or polymeric beads. Each variety of label has particular strengths and disadvantages. Parameters which must be evaluated in selecting a label include, detection sensitivity, interference by other assay components and sample medium, speed of signal generation, ease of labeling, multiplex capability, compatibility with a wide variety of analytes and assay formats, instrumental requirements for generating and/or detecting the signal, ease of automation, etc. New labeling and detection technologies are always in demand in order to address these needs and expand the testing market.

SUMMARY

This section provides a general summary of the disclosure and is not a comprehensive disclosure of its full scope or all of its features.

The present disclosure concerns methods, materials, electroluminescent light sources, and devices for producing electroluminescence in the service of a test method for determining the presence or amount of a target species in a sample. The methods rely on one or more specific binding reactions between specific binding partners. Binding reactions cause an electroluminescent nanoparticle label to be brought into operable proximity to one or more pairs of electrodes. Application of an electrical excitation signal to the electrode/nanoparticle system in the presence of a liquid medium generates light for detecting the presence or amount of a target species.

In one embodiment, an electroluminescent nanoparticle label is utilized in a light source that produces light in a liquid medium. The light source includes: a support member; a liquid medium supported by the support member, at least one pair of electrodes disposed proximate to the support member; and an excitation source electrically coupled to the pair of electrodes. In one embodiment, the electrodes are arranged coplanar with each other and a surface of each electrode in the pair of electrodes is in direct contact with nanoparticles, where the nanoparticles are comprised of a luminescent material and are overlaid by the liquid medium. The excitation source operates to apply an excitation signal between the electrodes in the pair of electrodes.

In some embodiments, the electrodes are coated with or otherwise separated from the liquid medium by a dielectric material.

In some embodiments, the electrodes are coplanar and are disposed on a surface of a solid support. Multiple electrically connected pairs of electrodes may be used to provide a larger surface area. Such electrodes may be interdigitated electrodes (IDEs).

Nanoparticles may take many different forms. For example, the nanoparticle may be comprised of one or more of an elemental semiconductor such as silicon or germanium, a metal chalcogenide, a group IIB-VI semiconductor compound or a group III-V semiconductor compound. The nanoparticles may be doped, for example with dopants chosen from transition metals or rare earth metals. In some example, the nanoparticles may be embedded into a solid phase matrix, where the solid phase matrix is selected from a group comprised of silica gel, cross-linked dextran gel, zeolites and molecular sieves. It is understood that the nanoparticles may include two or more different types of luminescent materials.

In some embodiments, the liquid medium is polar and may be selected from a group consisting of water, dimethyl sulfoxide, and dimethylformamide. The liquid medium may also include electrolytes, buffer materials, or other enhancing elements.

In one embodiment, the support member is a plate and the liquid medium is disposed on a surface of the plate. In another embodiment, the support member is a container configured to hold the liquid medium and the pair of electrodes are integrated onto an inner surface of the container.

In operation, the excitation source generates an electric current between the electrodes in the pair of electrodes. In one embodiment, the excitation source applies a voltage between the electrodes in the pair of electrodes, where polarity of the voltage periodically changes from positive to negative and vice versa. In some embodiments, the pulses of voltage applied between the electrodes are separated by a period of time in which the magnitude of the voltage is a baseline value that is less than peak value of the pulses.

Further areas of applicability will become apparent from the description provided herein. The description and specific examples in this summary are intended for purposes of illustration only and are not intended to limit the scope of the present disclosure.

BRIEF DESCRIPTION OF THE SEVERAL VIEWS OF THE DRAWING

The drawings described herein are for illustrative purposes only of selected embodiments and not all possible implementations and are not intended to limit the scope of the present disclosure.

DETAILED DESCRIPTION

Figure 1:
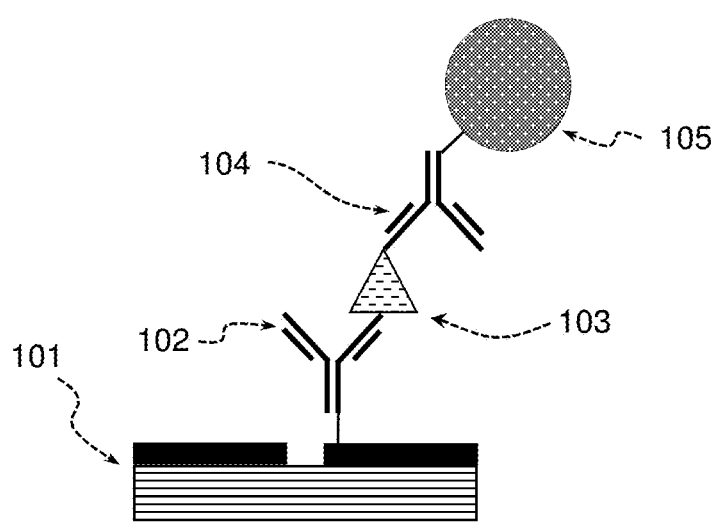
FIG. 1 is a diagram depicting an example embodiment of an electroluminescent sandwich immunoassay as described in Example 3.

Example embodiments will now be described more fully with reference to the accompanying drawings.

Definitions

Analyte (or Target Species)—refers to the compound or composition to be detected and is used interchangeably with target species. Analyte includes any compound or aggregate of interest to detect and/or label. Non-limiting examples of analytes include a protein, peptide, carbohydrate, polysaccharide, glycoprotein, nucleic acid, lipid, hormone, receptor, antigen, allergen, antibody, drug, pharmaceutical, nutrient, toxin, poison, explosive, pesticide, chemical warfare agent, biohazardous agent, vitamin, waste product, contaminant or other molecule. The analyte can itself be a member of a specific binding pair (sbp) and may be a ligand, which is monovalent (monoepitopic) or polyvalent (polyepitopic), usually antigenic such as avidin and streptavidin. The analyte can be a part of a cell such as bacteria or a cell bearing a blood group antigen such as A, B, D, etc., or an HLA antigen or a microorganism, e.g., bacterium, fungus, protozoan, or virus. The term analyte also includes receptors that are polynucleotide binding agents, and the like. The term analyte is intended further to encompass any type of cell, cellular component or tissue.

Analog of an Analyte or Target Species—means a substance which shows similar behavior to the substance to be assayed in a binding reaction with a specific binding substance. In general, it means a substance which is structurally analogous to the substances to be assayed. Illustrative examples include various types of structural analogues of the substances to be assayed. In the present disclosure, these structural analogues will typically bear a nanoparticle label as exemplified below, mainly when a substance to be assayed has a low molecular weight and its specific binding reaction is employed in a competitive assay method.

Ligand—as used in the present disclosure indicates a substance for which there is a specific binding. The ligand usually is a peptide, polypeptide, protein, carbohydrate, glycoprotein, steroid, or other organic molecule for which a specific binding partner exists in biological systems or can be synthesized. The ligand, in functional terms, is usually selected from the group comprising antigens and antibodies thereto; haptens and antibodies thereto; and hormones, vitamins, metabolites and pharmacological agents, and their receptors and binding substances. Usually, the ligand is an immunologically-active polypeptide or protein of molecular weight between 1,000 and 10,000,000, such as an antibody or antigenic polypeptide or protein, or a hapten of molecular weight between 100 and 1,500.

Linker, Linking Group—a linker refers to a divalent or higher valent moiety used for the covalent linkage between molecules, substances such as particles, or surfaces. Linkers will possess at least two linking groups that provide sites of attachment, typically covalent attachment. The linking group will vary depending upon the nature of the molecules or objects being joined, a specific binding pair member or the molecule associated with or part of a particle, being linked. The linker comprises functional linking groups that are normally present or are introduced synthetically when employed for linking these molecules to a specific binding partner or to a particle or nanoparticle as described in the present disclosure.

Operable Proximity—as used in the present disclosure indicates a spatial and functional relationship between electrodes and the electroluminescent nanoparticles. Nanoparticles can be considered to be in operable proximity to the electrodes by being physically on the electrodes, in the region between the electrodes, or at a distance perpendicular to the plane containing the electrodes that permits sufficient electrical stimulation to generate luminescence. In some embodiments, proximity can be from 0-about 100 nm or from 0-about 50 nm. In other embodiments, especially if a capture particle having a diameter of up to about 1 µm is used, proximity can be from 0-about 5 µm.

Sample—materials upon which the methods of the present disclosure are performed to detect an analyte and includes human and animal bodily fluids, such as blood, serum, urine, saliva, sputum, CSF, seminal fluid and cell lysate, as well as food samples, water samples, plant samples, microbiological specimens and forensic specimens. Other types of samples as would occur to one of ordinary skill in the art are considered to be within the scope of the disclosure. Typical samples are liquid materials which contain or are suspected to contain a substance to be assayed. Also included are solid, gel or sol substances such as mucus, body tissues, cells and the like suspended or dissolved in liquid materials such as buffers, extractants, solvents and the like.

Solid support-test medium on which assay methods of the present disclosure can be carried out. Such supports include test strips, blotting membranes, filters, microwells, test tubes, beads and the like as are known in the art of assays. The supports must be capable of capturing or immobilizing the target species-specific binding agent pair by physical adsorption or covalent linkage or both.

Specific binding pair (sbp) member—refers to one of two different molecules or portions thereof which have a specific binding affinity for one another by virtue of multiple non-covalent attractions. Such molecules have an area on the surface or in a cavity which specifically binds to and is thereby defined as complementary with a particular spatial and polar organization of the other molecule. The members of the specific binding pair are sometimes referred to as ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the disclosure and the definition of sbp member.

The present disclosure concerns methods, materials, electroluminescent light sources, and devices for producing electroluminescence in the service of a test method for determining the presence or amount of a target species in a sample. The methods rely on one or more specific binding reactions between specific binding partners.

In one embodiment, there is provided a method for detecting a target species in a sample suspected of containing the target species by producing electroluminescence in a liquid medium comprising:
  (a) providing a solid support having disposed thereon at least one pair of electrodes to which is immobilized a first specific binding partner which is capable of binding to the target species;
  (b) providing an electroluminescent nanoparticle label as a conjugate, wherein the nanoparticle is bound to either an analog of the target species or to a second specific binding partner of the target species;
  (c) combining the sample and the electroluminescent nanoparticle conjugate in a liquid medium to form a mixture;
  (d) applying the mixture to the solid support to specifically bind the target species to the first specific binding partner and thereby bring the electroluminescent nanoparticle conjugate into operable proximity to the electrodes;
  (e) removing all materials not bound to the solid support;
  (f) applying a time-varying excitation signal between the electrodes in the pair of electrodes in the presence of added liquid medium with an excitation source electrically coupled to the pair of electrodes, thereby exciting the nanoparticles to produce electroluminescence; and
  (g) detecting the electroluminescence produced while the electrical excitation is being applied, wherein the presence of electroluminescence indicates the presence of the target species in the sample.

In another embodiment, target species and target species analogs if present are first captured on a capture particle and the resulting complexes are drawn to and immobilized onto a solid support containing electrode pair(s).

In one embodiment, there is provided a method for detecting a target species in a sample suspected of containing the target species by producing electroluminescence in a liquid medium comprising:
  (a) providing a solid support having disposed thereon at least one pair of electrodes;
  (b) providing a capture particle conjugate comprising a particle bound to a first specific binding partner of the target species;
  (c) providing an electroluminescent nanoparticle label as a conjugate, wherein the electroluminescent nanoparticle is bound to either an analog of the target species or to a second specific binding partner of the target species;
  (d) combining the sample, the capture particle conjugate, and the electroluminescent nanoparticle conjugate in a liquid medium to form a mixture for a time sufficient for specific binding to occur, thereby associating the electroluminescent nanoparticle with the capture particle;
  (e) immobilizing the capture particle conjugates onto the solid support to thereby bring the electroluminescent nanoparticle conjugate into operable proximity to the electrodes;
  (f) removing all materials not bound to the solid support;

(g) applying a time-varying excitation signal between the electrodes in the pair of electrodes in the presence of added liquid medium with an excitation source electrically coupled to the pair of electrodes, thereby exciting the nanoparticles to produce electroluminescence; and (h) detecting the electroluminescence produced while the electrical excitation is being applied, wherein the presence of electroluminescence indicates the presence of the target species in the sample.

Assay Method

The electroluminescent methods of the present disclosure can be used in specific binding heterogeneous assays. Such exemplary methods may be conducted under one of two broad categories, the sandwich format or the competitive format.

In the sandwich format, assays employ a first binding reagent, e.g., an antibody, that has been labeled with a luminescent substance and a second binding reagent, e.g., a second antibody, that serves as a capture reagent. In this format, both the first and second binding reagents are capable of binding simultaneously to the analyte of interest, at different locations or epitopes. The second binding reagent is immobilized on a solid support. The immobilization may be accomplished by bonding the second binding reagent and the solid support either directly or through a third binding reagent that is immobilized on the solid support. When the latter embodiment is used, the reactions of the first and second binding reagents with the analyte may occur before the solid support is introduced to the sample, in which case, those reactions behave substantially in accordance with solution reaction kinetics. Alternatively, all of the components may be added at the same time, in which case the binding reactions occur simultaneously.

The complex formed by the reaction of the first and second binding reagents with the analyte is separated from unbound labeled binding reagent by separating the solid support from the sample mixture. In one embodiment of this disclosure, the second binding reagent is immobilized on capture particle which may be magnetic particles, either directly or indirectly through an immobilized third binding reagent. The separation step may involve either removal of the particles from the sample or localization of the particles within the sample to allow the detection of luminescence.

In the competitive assay format, the first binding reagent is not used. The immobilized second binding reagent which is capable of binding with the analyte of interest is combined with the sample or calibration standard and a fixed amount of analyte that has been labeled with electroluminescent nanoparticle. Unlabeled analyte in the sample or standard competes with labeled analyte for the immobilized binding reagent. The amount of labeled analyte that binds to the immobilized binding reagent is inversely proportional to the amount of analyte in the sample or standard. Therefore, the intensity of the luminescence produced in a given assay is inversely related to the amount of the analyte in the sample. As in the sandwich format, the second binding reagent may be bound directly to the solid support or may be capable of binding to a third binding reagent that is immobilized on the solid support as described above.

Antibodies used in the practice of the present methods may, for example, be a polyclonal, monoclonal or a binding fragment thereof, e.g., Fab, Fab' or F(ab')$_2$ fragment, or a synthetic single-chain antibody.

When used to perform a nucleic acid hybridization assay for detection of a DNA or RNA analyte, the present methods can be designed according to art-known binding formats. In one embodiment a labeled analyte is captured with immobilized sequence specific probe. In another embodiment a labeled analyte is labeled analyte having a universal sequence such as the polyA tail on RNAs captured with immobilized universal capture probe. In another embodiment a target sequence is hybridized to a first sequence specific probe immobilized on or near the electrode and with a second sequence specific probe labeled with the nanoparticle. Large nucleic acid analytes can bind multiple nanoparticle-labeled probes to provide additional label for greater signal. Branched DNA multimer probes bearing a plurality of nanoparticle labels can also be used to increase the amount of signal. Several different probes bearing different nanoparticles emitting different color light can be utilized together in a multiplex format.

In additional embodiments, the binding reagent may be another molecule that participates in a specific binding reaction, e.g., a hormone, a receptor, an enzyme, a binding protein such as folate binding protein or intrinsic factor, a substrate, an immunoglobulin binding protein, such as protein A or protein G, and the like. The first binding reagent has a binding affinity for the analyte of interest.

Embodiments where quantitation is desired will involve measuring the amount of light and relating the amount of light produced to the amount of the analyte. The relationship between light intensity and amount of analyte can be easily discerned by, for example, constructing a calibration curve with known amounts of the analyte.

The binding reactions in an assay for the analyte will normally be carried out in an aqueous solution at a moderate pH which provides optimum assay sensitivity, preferably from 4-10, and more usually from about 6-8. The aqueous solution may be solely water or may include from 0.01 to 80 volume percent of a co-solvent but will usually include less than 40% of a co-solvent when a sbp member is used that is a protein. The pH for the medium of the binding reaction will usually be in the range of about 6.5 to 9.5. The pH will usually be a compromise between optimum binding of the binding members and the stability of other reagents of the assay.

The order of addition of components can vary depending on the nature of the assay. The simplest order of addition is to add all the materials simultaneously. Alternatively, the reagents can be combined wholly or partially sequentially. When the assay is competitive, it will often be desirable to add the analyte analog after combining the sample and an sbp member capable of binding the analyte. Optionally, an incubation step may be involved after the reagents are combined, generally ranging from about 30 seconds to 6 hours, more usually from about 2 minutes to 1 hour, dependent on other factors such as temperature and the nature of the particular materials. Wash steps and separation steps using, for example, centrifugation will also be useful in some embodiments of the present method as demonstrated in the examples below. For example, capture particles, when used, can be washed before immobilization onto the solid support or after immobilization.

In carrying out an assay utilizing the present device, the protocol will normally involve combining in an aqueous solution the sample suspected of containing the analyte and other reagents as necessary for the assay protocol chosen to form a test solution. In some instances, the test solution will be the sample itself. The sample may be derived from a wide variety of sources, such as physiologic fluids, illustrated by saliva, blood, serum, plasma, urine, ocular lens fluid, spinal fluid, etc., food products such as milk and wine, chemical processing streams, food waste water, any type of cell, cellular component or tissue.

Electroluminescent Particles

In some embodiments, solid state electroluminescent nanoparticles are suspended in the liquid medium. In one embodiment, the electroluminescent nanoparticles are defined as nanoparticles having dimensions less than 1000 nm. In other embodiments, the electroluminescent nanoparticles are further defined as nanoparticles having dimensions less than 100 nm. In other embodiments, the electroluminescent nanoparticles may be core-shell nanoparticles having characteristic dimensions less than 100 nm. In other embodiments the electroluminescent nanoparticles will range in size from about 5-50 nm.

The solid state luminescent materials may be chosen from elemental or composite semiconductor materials. For example, the elemental semiconductors may be silicon and/or germanium nanoparticles. In another example, compound semiconductors may be chosen from group IIB-VI element compositions, such as ZnO, ZnS, ZnSe, CdS, CdSe, and CdTe. Composite structures such as nanoparticles having a CdSe core with ZnS shell are also contemplated by this disclosure. In yet another example, compound solid state luminescent materials may be chosen from group III-V elements like GaAs, as well as group IV-VI elements like PbS.

In some embodiments, the luminescent materials may be doped to produce light emission having different colors or wavelengths. In general, transition metal elements as well as rare earth elements are useful as dopants. For example, ZnS nanoparticles doped with manganese (Mn) emit orange light; whereas, ZnS nanoparticles doped with copper (Cu) produce green light. In other examples, luminescent materials can be doped with samarium (Sm), thulium (Tm), erbium (Er), neodymium (Nd), europium (Eu), other lanthanide rare earth elements and other art-recognized types of dopants.

Electrodes

Electrodes may take different forms. In some embodiments, the pair of electrodes are coplanar. In the same or different embodiments, the electrodes can be interdigitated. The present methods may use a single pair of electrodes or multiple pairs of electrically connected electrodes. The electrodes may be comprised of aluminum or aluminum alloys, gold, silver, copper, platinum, as well as other metals, metal alloys (e.g., indium tin oxide or fluorine-doped tin oxide), semiconductor materials, or other types of conductive materials, such as glassy carbon, graphite and graphene.

In some embodiments, the electrodes can be coated or otherwise separated from the liquid medium by a dielectric material. Example dielectric materials include but are not limited to silicon nitride, silicon oxide, aluminum oxide, Pyrex, polystyrene, polymethyl methacrylate, polytetrafluoroethylene, polydimethylsiloxane. It is noted that the manufacture of certain metallic electrodes spontaneously results in the presence of a coating due to exposure to air. Other types of dielectric and insulating materials are also contemplated by this disclosure.

In many example embodiments, the pair(s) of electrodes are integrated into a support structure such as a planar surface such comprised of glass, or into the floor or bottom surface of a container. Electrodes could alternatively be fabricated into the walls of tubes, the bottoms of microtiter wells, or other higher density (384 and 1536 well) plates.

Liquid Media

The detection reaction of the present disclosure is carried out in a liquid medium which is in contact with the surface of a solid support containing the electrodes. In some embodiments, the liquid medium is a polar liquid such as water or an aqueous solution, including buffers. Other polar liquid media include, for example, dimethyl sulfoxide and dimethylformamide. Use of mixed solutions is within the scope of the present disclosure.

In other embodiments, the liquid medium can be a nonpolar liquid. Exemplary nonpolar liquids include, without limitation, oils such as mineral oil, castor oil or linseed oil.

Other Liquids Used in the Method

In some embodiments, water or an aqueous solution is used during the step(s) which bring the binding reaction components to the solid supported electrodes. The aqueous solution can further comprise, buffer materials. Suitable buffers include any of the commonly used buffers capable of maintaining a pH in the range of about 4 to about 10 for example, phosphate, borate, acetate, carbonate, tris(hydroxymethylamino)methane, glycine, tricine, 2-amino-2-methyl-1-propanol, diethanolamine and the like. Aqueous solutions may further comprise salts, surfactants and other reagents commonly employed during performance of assay steps. The preferred method of practicing the disclosure in this regard is determined by the requirements of the particular intended us.

In some embodiments, wash solutions or wash buffers can be used. Such solutions are commonly known and used in the art to remove materials from the assay system. Typical wash buffers comprise an aqueous buffer and, optionally, a surfactant.

Analytes (Target Species)—refers to the compound or composition to be detected and is used interchangeably with target species. Analyte includes any compound or aggregate of interest to detect and/or label and must be capable of binding with a substance with which there is a specific binding affinity. Non-limiting examples of analytes include a protein, peptide, carbohydrate, polysaccharide, glycoprotein, nucleic acid, lipid, hormone, receptor, antigen, allergen, antibody, substrate, metabolite, cofactor, inhibitor, drug, pharmaceutical, nutrient, toxin, poison, explosive, pesticide, chemical warfare agent, biohazardous agent, prion, vitamin, heterocyclic aromatic compound, carcinogen, mutagen, narcotic, amphetamine, barbiturate, hallucinogen, waste product, or contaminant. The analyte can itself be a member of a specific binding pair including such materials as avidin, streptavidin and may be a ligand, which is monovalent (monoepitopic) or polyvalent (polyepitopic). The analyte can be a cell, a part of a cell, such as a blood group antigen such as A, B, D, etc., or an HLA antigen, a microorganism, e.g., bacterium, fungus, protozoan, or virus, phage, macrophage, or a tissue.

The term analyte further includes polynucleotide analytes such as those polynucleotides defined below. These include m-RNA, r-RNA, t-RNA, DNA, DNA-RNA duplexes, siRNA, XNA, PNA, aptamers and the like. Genetic sequences can represent the target species. The term analyte also includes receptors that are polynucleotide binding agents, such as, for example, restriction enzymes, nucleases, polymerases, histones, and the like.

Representative protein ligands include, for example, the classes of protamines, mucoproteins, glycoproteins, globulins, albumins, phosphoproteins, histones, lipoproteins, chromoproteins, and nucleoproteins. Examples of specific proteins are bovine and human serum albumins, hemoglobin, myoglobin, erythropoietin, transferrin, immunoglobulins such as IgG, IgM, IgA, IgD, and IgE, and their fragments, e.g., $F_c$ and $F_{ab}$, complement factors, prolactin, blood clotting factors, insulin, melanotropin, somatotropin, thyrotropin, follicle stimulating hormone, leuteinizing hormone, gonadotropin, thyroid stimulating hormone, serum enzymes such as, lactic dehydrogenase, amylase, lipase, phosphatases, cholinesterase, tissue antigens, bacterial antigens, and viral antigens such as hepatitis associated antigens (e.g., $HB_s$ Ag, $HB_c$ Ag and $HB_e$ Ag).

Representative hapten ligands include the general classes of drugs, metabolites, hormones, vitamins, and the like organic compounds. Haptenic hormones include thyroxine and triiodothyronine. Vitamins include vitamins A, B, e.g., $B_{12}$, C, D, E and K, folic acid and thiamine. Drugs include antibiotics such as aminoglycosides, nucleosides and nucleotides such as adenosine diphosphate, adenosine triphosphate, flavin mononucleotide, nicotinamide adenine dinucleotide and its phosphate derivative, thymidine, guanosine and adenosine; prostaglandins; steroids such as the estrogens, sterogens, androgens, digoxin, digitoxin, and adrenocortical steroids; and others, for example, phenobarbital, phenytoin, carbamazepine, theophylline, caffeine, propanolol, cortisol, amphetamines, and antihistamines.

Specific Binding Pairs (SBP)

A specific binding pair member or partner includes a substance which has a specific affinity for a certain other substance such as a substance to be assayed. Examples of combinations of the specific substance with the specific binding substance include: antigens with corresponding antibody molecules, avidin-biotin, streptavidin-biotin, hormone-receptor, a nucleic acid sequence with its complementary sequence, nucleic acid-nucleic acid binding protein, nucleic acid-anti-nucleic acid antibody effector molecules with receptor molecules, enzymes with inhibitors, sugar chain-containing compounds with lectins, an antibody molecule with another antibody molecule specific for the former antibody, receptor molecules with corresponding antibody molecules and the like combinations.

When nucleic acid probes are employed in the practice of the present methods the probe length may be any suitable length which provides specific binding and is capable of bearing at least one label. Synthetic oligonucleotide probes can be from about 10-200 bases, more commonly 15-50 bases. Probes produced by cloning can be up to a few thousand bases in length. In general, shorter probes of 20-25 bases provide better specificity and longer probes of several hundred bases long increase the sensitivity because of the ability to attach more labels. Methods of probe production and labeling are generally known in the art.

Specific binding substance—means a substance which has a specific affinity for a certain substance such as a substance to be assayed, that is, a substance which is capable of undergoing a specific binding reaction with a specific substance. Examples of combinations of the specific substance with the specific binding substance include: antigens with corresponding antibody molecules, a nucleic acid sequence with its complementary sequence, effector molecules with receptor molecules, enzymes with inhibitors, sugar chain-containing compounds with lectins, an antibody molecule with another antibody molecule specific for the former antibody, receptor molecules with corresponding antibody molecules and the like combinations. Other examples of the specific binding substances include a compound which has been chemically modified to such a degree that its specific binding activity still remains intact and a complex body of a compound bound to other components. Examples of combinations of such types of specific binding substances with the specific substances include: a chemically biotin-modified antibody molecule or polynucleotide with avidin, an avidin-bound antibody molecule with biotin and the like combinations.

Conjugation of Linking Groups and Assay Components

Selection of the binding component for a particular assay and the means for incorporating sbp members into the labeled conjugate are matters of ordinary skill in the art. In choosing the sites of attachment to a sbp member, the important considerations are (1) preservation of the ability of the linked sbp member to participate effectively in the selected binding assay system, (2) convenience and yield of synthesis and purification. Usually, the linking group will comprise a chemical bond, usually a single, but sometimes a double bond, or a chain containing between 1 to 100, more commonly 1 to 50 or 1 to 10, carbon atoms and 0 to 10, more commonly 1 to 5, heteroatoms selected from nitrogen, oxygen, and sulfur. In one embodiment, poly(oxyethylene) chain compounds, commonly known as PEGs are used as linkers. The atoms in the chain may be substituted with atoms other than hydrogen in a manner similar to that described for organic groups. As a general rule, the length of a particular linking group can be selected arbitrarily to provide for convenience of synthesis, minimize interference of binding sbp members, and permit the attachment of any desired group.

Frequently, carbonyl functionalities are useful as linking groups, including groups such as aldehydes, acetyl, amides and carboxy groups; and non-oxocarbonyl groups, including nitrogen and sulfur analogs, such as amidine, amidate, thiocarboxy and thionocarboxy. Alternative linking groups, such as halogen, diazo, mercapto, olefin (particularly activated olefin), amino, phosphoro, siloxy and the like may also be used. A good description of linking groups may be found in standard treatises such as *The Immunoassay Handbook, Theory and Applications of ligand binding, ELISA and related techniques,* $4^{th}$ ed., Elsevier, David Wild (2015), Chapter 3.4.

A sbp member may be physically adsorbed on the surface of the electroluminescent nanoparticles, capture particles such as magnetic particles, solid supports or electrodes or may be covalently bonded thereto. It is usually preferable to covalently bond sbp members to the surfaces. This may be accomplished by chemically activating the surface. For example, the N-hydroxysuccinimide (NHS) ester of surface carboxyl groups can be formed and the activated particles are then contacted with a linker having amino groups that will react with the ester groups or directly with an sbp member that has an amino group. The linker will usually be selected to reduce nonspecific binding of assay components to the particle surface and will preferably provide suitable functionality for both attachment to the nanoparticle or electrode and attachment of the sbp member.

Uses and Applications of the Present Methods

The methods of the present disclosure find many areas of applicability. Immunoassay technology in particular has been employed to detect and quantify analytes in a variety of fields. In the area of medical and veterinary testing, existing assays monitor, for example, steroids, endocrine hormones, cardiac markers for diagnosing heart attacks, therapeutic drug monitoring, and screening for drugs of abuse. Home pregnancy test kits are in widespread use in consumer testing as are tests in sports doping testing. Environmental analytical uses include testing for pollutants and ground water contaminants, or agricultural pesticide run-off. The present methods are readily applicable to all of these uses. Lastly it is envisioned that the nanoparticle labels might serve as the basis for dual format assays when coupled with surface plasmon resonance or photoacoustic assay technologies.

It is another object of the present disclosure to provide an electroluminescent method for the detection by a sandwich immunoassay of protein antigens presenting at least two epitopes. Sandwich immunoassays are well known in the art. Heterogeneous sandwich immunoassays involve the use of a first antibody (capture antibody) immobilized on a solid phase which binds to a first epitope on the analyte. A second antibody binds to a second epitope of the analyte to form the so-called sandwich. To adapt the electroluminescent detection methods of the present disclosure to this type of assay, requires that one antibody be labeled with an electroluminescent nanoparticle.

Another particularly useful application of the present detection methods is the detection of nucleic acids by the use of nanoparticle-labeled nucleic acid probes. Methods for analysis and detection of nucleic acids, for example, hybridization assays, DNA amplification by Northern blotting, qPCR, DNA sequencing, DNA fingerprinting, the study and detection of mutations for genetic disorders or for microbial characterization, tissue typing, cancer screening, paternity testing, genealogical characterization of ancestry are all well-established techniques. Application of the present methods to these fields and techniques is considered to fall within the scope of the present inventive methods.

The nanoparticle label can be present as a direct conjugate with a probe oligonucleotide or capture oligonucleotide or it can be incorporated through indirect linking means using art-known methods. Examples of indirect linking means include using hapten-labeled oligonucleotides and anti-hapten-particle conjugates or biotinylated oligonucleotides and avidin-particle conjugates. Exemplary haptens for which commercially available kits containing antibodies and labeling protocols are available include fluorescein, digoxigenin and dinitrophenol moieties.

Other ligand binding assays include cell surface receptor-ligand assays and real-time cell-binding assays. In this type of assay, the binding of a ligand to cells is followed over time. Signal is proportional to the number of ligands bound to a target structure, often a receptor, on the cell surface. Information about the ligand-target interaction is obtained from the signal change over time. In one embodiment cells are immobilized on a solid support at or near the electrodes and used to bind nanoparticle-labeled ligands. In an alternative embodiment, cells can bind nanoparticle-labeled ligands in solution and electrode-bound second capture ligands can be used to immobilize the labeled cells.

Flow assays as are generally known in the art, including lateral flow assays and methods involving microfluidic and capillary-based flow systems are considered to be adaptable to methods of the present disclosure.

Form and Generation of Electrical Signal

Light is thought to be produced from the recombination of electric charges of opposing polarity in or on the luminescent materials. The luminescent materials dispersed in the liquid medium produce light when the liquid wets the electrodes and the electrodes are energized by a power source. An excitation signal is generated between the electrodes and may take different forms. It is known that applying an excitation electrical stimulus in the form of a constant DC voltage applied between the electrodes produces flashes of light from the excited luminescent nanoparticles. However, it is desirable to produce a longer-lasting more continuous light emission. In some embodiments then, the magnitude of the applied voltage is periodically changed from a first value to a second value, for example from positive to negative and vice versa. The varying voltage may have different waveforms including but not limited to sine, square, triangle, and sawtooth waveforms. In some embodiments, combinations of these waveforms may be used.

In other embodiments, the pulses of voltage may be separated by a period of inactive sleep time. Voltage pulses have magnitudes that oscillate between a peak positive value and a peak negative value. During the sleep period, the magnitude of the voltage is set at a baseline value that is less than the peak value of the pulses. For example, the baseline value may be zero or another nominal value, such as ±one volt. This feature is useful for reducing input power, minimizing gas evolution due to electrolysis and extending the life of the electrodes. The percentage sleep time can also be used to modify the intensity of light emission. In yet other embodiments, the excitation waveform may be modulated according to a second waveform. For example, the excitation waveform may be modulated such that the peak value of the voltage pulses applied between the electrodes varies over time. In another example, the excitation waveform may be modulated such that frequency of the pulses varies over time. This enables excitation of luminescent nanoparticles across a broad range of amplitude and frequency of the periodic electrical stimulus.

In some embodiments, voltage will be varied with a frequency ranging from 1 Hz to 1 kHz or from about 40 Hz to about 300 Hz. In some embodiments, voltages in the range of 10 V to 1000 V peak-to-peak or from 10 V to 500 V depending on the electrode and nanoparticle material. Dielectric-coated gold electrodes are used at voltages near the higher end of these ranges. In some embodiments, a cycle sleep time will be used ranging from 0-99% of the cycle and in some embodiments from 80-99% of the cycle. In some embodiments, the method will use an electrical stimulation time ranging from 0.1-60 s or from 0.1-30 s or from 0.1-10 s.

Detection of Light for Detecting the Presence or Amount of Analyte

The electroluminescent methods of the present disclosure generate light at wavelengths, more accurately ranges of wavelengths, governed by the emissive properties of the electroluminescent nanoparticles used. In general light is produced in a region of the electromagnetic spectrum spanning the ultraviolet, visible and near infrared wavelengths. One or more colors of light can be generated in the methods of the present disclosure by deliberate choice of nanoparticles.

Electroluminescent light produced in the present methods may be detected by any suitable means and is not limited to any particular mode of detection or visualization. Light produced in the visible portion of the spectrum can be detected by eye, for example. Other means of detecting the emitted light include digital cameras, photographic film, CCD chips, CMOS chips, and sensor arrays. Commercial or purpose-built luminometers also can be used to detect and measure the electroluminescence produced in the present methods. Luminometers having a measurement chamber designed to house a single sample tube such as a Turner Designs TD 20/20 or similar can be used. Alternatively, luminometers designed to receive a 96-well microplate and measure each of the wells can also be used. In some embodiments it may be desirable to select a portion of the wavelengths of light emitted. In such cases the method may further comprise the use of monochromators (prism or grating), or optical filters including low-pass, high-pass and notch or band-pass filters. Optical systems including microscopes using a variety of lenses for optical magnification and selecting a plane of focus can be used in some embodiments.

Detecting a target species can take the form of a quantitative assay for determining the amount of the target species in the sample. The detection can also be qualitative in nature in which case a simple yes/no type of answer can be obtained. The methods of the present disclosure can also be employed in a test to determine the location of an analyte or target species since the enzyme labels are localized or immobilized in a region of space.

Kits—Another aspect of the present disclosure relates to kits useful for conveniently performing an assay method of the disclosure for determining the presence or amount of an analyte in a sample suspected of containing the analyte. Kits for performing the methods of the present disclosure may provide reagents—linkers, nanoparticles, antibodies, probes, binding partners, buffers, wash solutions, calibrators, etc.—in packaged combination, in the same or separate containers, so that the ratio of the reagents provides for substantial optimization of the method and assay. The reagents may each be in separate containers or various reagents can be combined in one or more containers depending on the cross-reactivity and stability of the reagents.

These and other embodiments of the present disclosure will readily occur to those of ordinary skill in the art in view of the disclosure herein.

EXAMPLES

The following examples are described to illustrate, not to limit, the scope of the disclosure.

Data Processing:

The images of the system of this disclosure were processed in some embodiments to obtain numerical values for the intensity of the emitted light. ImageJ software was used for analysis of the captured images. The average intensities for each sample was extracted from the software output and the numerical values were later used for making plots or further interpretation of the data.

Example I: Activation of the Electrodes

The interdigitated electrodes (IDEs) as described in U.S. patent application serial number 20170064792A1, entitled "Coplanar Electrode Arrangement for Electroluminescent Devices" which is incorporated by reference herein can be applied as the substrate for performing the method of this disclosure. The IDEs were cleaned with ethanol and air dried. Clean IDEs were submersed in a solution of (3-aminopropyl)triethoxy silane (99% Aldrich, 2% V/V solution in acetone) for 5 min, following by rinsing the IDEs with acetone (HPLC grade, Fisher Chemical). The IDEs were air dried. In the next step the IDEs were washed with a wash buffer three times and were rinsed with phosphate buffer saline (0.1 mM phosphate buffer saline, pH 7.4, Fisher Scientific; hereafter called PBS). The wash buffer was PBS containing 0.05% V/V Tween 20 (polyoxyethylene sorbitan monolaurate, Fisher Scientific; hereafter called wash buffer). The activated IDEs (hereafter called IDE-NH$_2$s) were dried and used for the next steps of the process.

In some embodiments, the activated surface of IDE is comprising functionalizing the surface of the IDEs with carboxyl groups (IDE-COOH) and use the IDE-COOH as a template for conjugation of biomolecules through different conjugation techniques. In one example to prepare IDE-COOH, 50 µL of mercaptopropionic acid solution (MPA, 99.0%, Sigma-Aldrich, 0.4 M solution in DI water) was added over the IDE so it covers the surface of the IDE and was incubated at room temperature overnight.

After the incubation, the IDE-COOH was washed with DI water.

Example 2: Preparation of Electroluminescent Nanoparticle-Labeled Antibody

The steps for preparation of electroluminescent nanoparticles labeled antibody (hereafter called NPs-Ab) are described herein. A 30 µL portion of Mn-doped ZnS nanoparticles (50 nm particle size, 10 mg/mL) capped with 3-mercaptopropionic acid (MPA) was suspended in deionized (DI) water (1 mL). Ethyl-3-(3-dimethylaminopropyl)carbodiimide.HCl (EDC, Thermo Scientific, 30 µg/mL in DI water) 21 µL was added to the suspension and the suspension was mixed for 1 minute at room temperature. After 1 minute, 5 µL of N-hydroxysuccinimide (NHS, Aldrich, 260 µg/mL in DI water) was added to the suspension. The suspension was incubated for 15 minutes at room temperature. 2 µL of 2-mercaptoethanol (2ME, Aldrich, 1:1000 V/V solution in DI water) was added to the suspension to make a reaction mixture. 25 µL of anti-albumin (Bovine Serum) rabbit IgG fraction (Anti-BSA, Invitrogen, 2 mg/mL) was added to the reaction mixture and the reaction mixture was incubated for 2 hours at room temperature. Reaction mixture was centrifuged at 14000 RPM for 10 minutes and the supernatant was decanted. For the purification step, the precipitates were redispersed in PBS and centrifuged again at 14000 RPM for 10 minutes and the supernatant was decanted. The purification step was repeated for 3 times. After the last purification step, the precipitates were dispersed in 1 mL of PBS.

Figure 2:
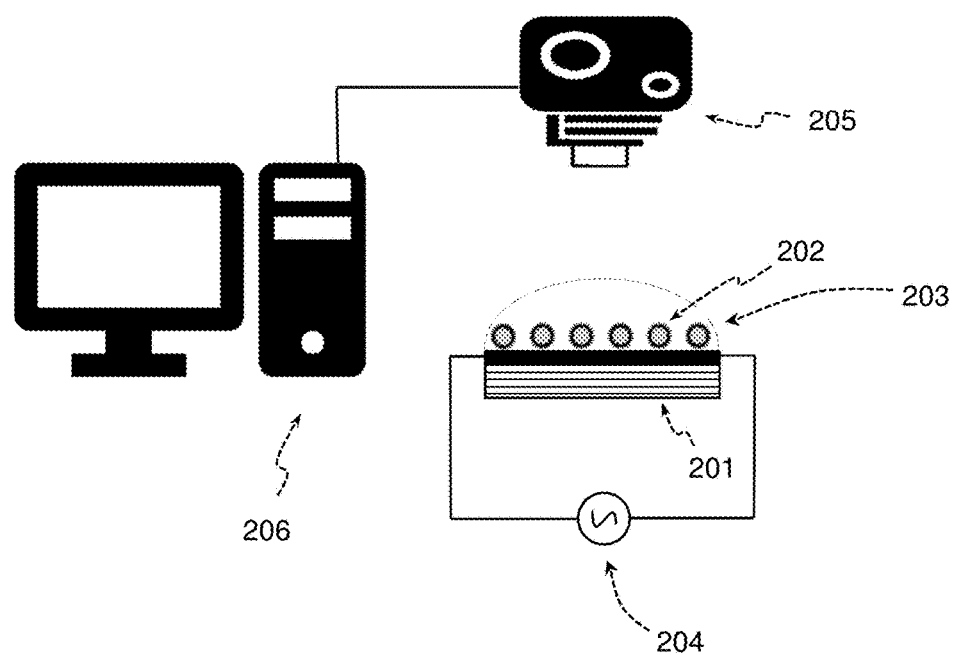
FIG. 2 is a diagram depicting an experimental system for collecting imaging data from the electroluminescent sandwich assay as described in Example 3. Nanoparticle-labeled analyte 202 in water 203 is deposited on electrodes 201 which are excited by a power source 204. Light emitted is captured by digital camera 205. Image files can be separately viewed and further processed by a personal computer.
Figure 10:
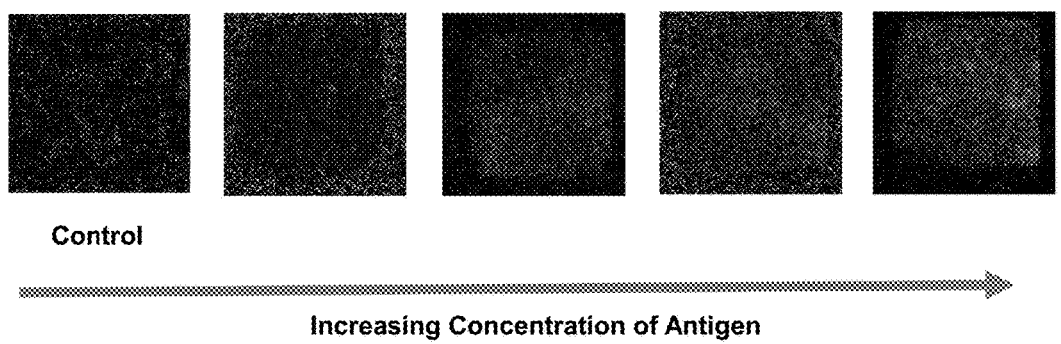
FIG. 10 depicts images from the sandwich immunoassay of Example 3.

Example 3 with Reference to FIGS. 1, 2 and 10: Mn-Doped ZnS Nanoparticle-Labeled Electroluminescent Sandwich Immunoassay for BSA A. Conjugating Second (Capture) Antibody on the Activated IDE The preparation of antibody conjugated electrodes (IDE-mAb) is described herein. 500 µL of DI water, 3 µg of monoclonal anti-Bovine Serum Albumin mouse IgG (mAnti-BSA) 102, 12 µL of EDC (3 µg/mL in DI water) and 3 µL of NHS (26 µg/mL in DI water) were added to a reaction tube to make solution A. Solution A was incubated for 15 minutes at room temperature. After 15 minutes, 30 µL of solution A was spread on the IDE-NH$_2$ 101. The electrodes were incubated on an orbital shaker at room temperature for 2 hours. After 2 hours the electrodes were washed 3 times with wash buffer and rinsed with PBS.

B. Blocking the non-specific binding sites 20 µL of blocking buffer (Pierce Clear Milk Blocking Buffer, 1× solution in DI water) was added to each IDE-Ab. The electrodes were placed on an orbital shaker and incubated at room temperature for 1 hour. After the incubation, the electrodes were washed 3 times with wash buffer and rinsed with PBS.

C. Adding the Antigen-Containing Sample to the Blocked IDE-mAb

10 µL of Bovine Serum Albumin solution (BSA, 98% Sigma, 10 mg/mL solution in PBS) 103 was added to 990 µL of PBS and labeled as first analyte solution. Second analyte solution to fifth analyte solution were prepared by serial dilution of the first analyte solution. A PBS solution was labeled as blank solution. Blank sample was prepared by adding 20 µL of the blank solution to a blocked IDE-Ab. First to fifth analyte samples were prepared by adding 20 µL of the first to fifth analyte solutions to blocked IDE-Abs, respectively. The electrodes were incubated at room temperature on an orbital shaker for 1 hour. After the incubation, the electrodes (IDE-mAb-BSA) were washed 3 times with wash buffer and rinsed with PBS.

D. Adding the Detection Antibody

20 µL of NPs-Ab of Example 2 (104-105) was added to each IDE-mAb-BSA, and was incubated at room temperature on an orbital shaker for 1 hour. After the incubation, the electrodes (IDE-mAb-BSA-Ab-NPs) were washed 3 times with wash buffer and rinsed with PBS and DI water. The IDE-mAb-BSA-Ab-NPs then were dried.

E. Imaging

FIG. 1 depicts a diagram of the typical imaging apparatus used for data collection. The IDEs 201 were secured on a holder and placed inside a dark box with a built-in camera 205 on top of the dark box. 20 µL of DI water 203 was placed over the IDE, and nanoparticles 202 so that the DI water covers the whole active surface of the electrode. A time-varying voltage having a square wave profile with a frequency of 57 Hz with 90% sleep/cycle and peak-to-peak amplitude of 60 V was applied to the IDEs by a power source 204. A digital camera was used for imaging the electroluminescence signal. Images were exposed for 60 s. Image data was sent to and processed by personal computer 206. It should be noted that the present system limits the scale of light intensities that can be measured to a range of 0-255 or slightly over two orders of magnitude. Other imaging systems and detectors in common use in assays involving light emission and detection feature a much wider dynamic range of measurement which often translates to higher detection sensitivity and a substantially broader assay range. It is fully expected that use of such detection equipment will afford significantly expanded assay dynamic range and improved assay sensitivity in the present assay methods.

Digital images of each of the serial dilutions of analyte processed in accordance with the above protocol are shown in FIG. 10.

Figure 3:
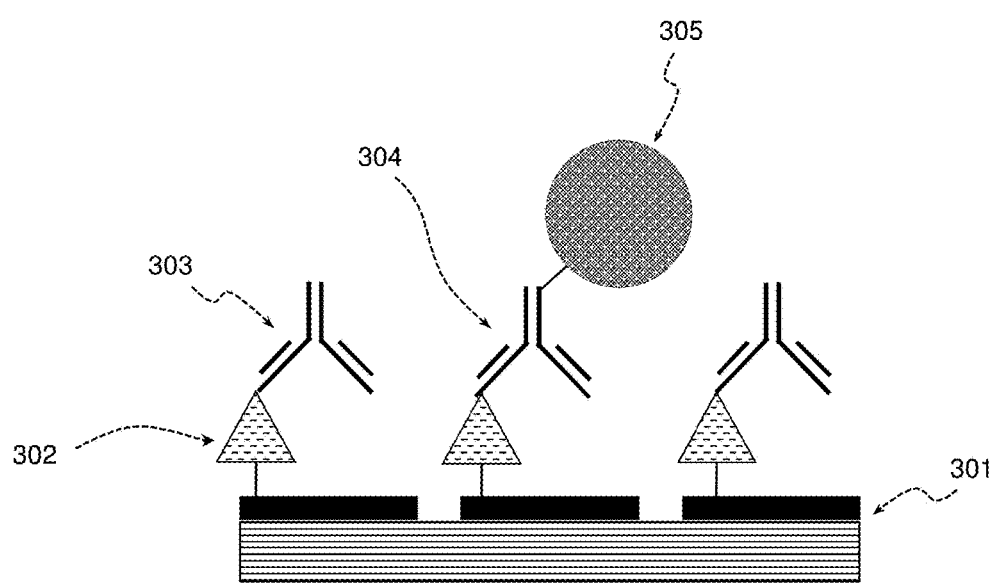
FIG. 3 is a diagram depicting an example embodiment of an electroluminescent competitive immunoassay as described in Example 4.
Figure 11:
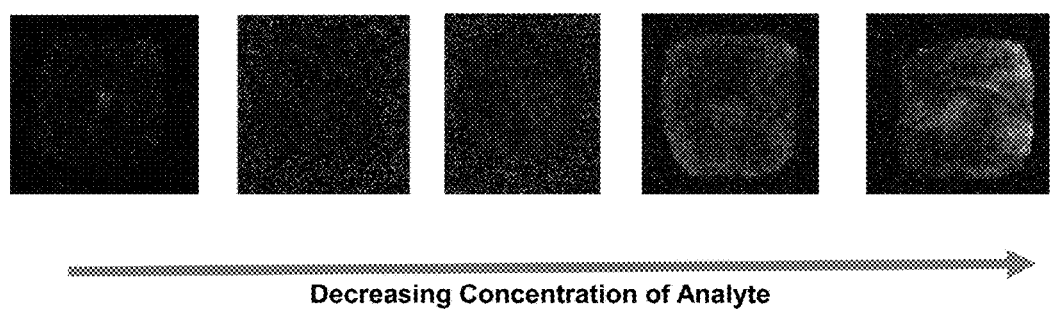
FIG. 11 depicts images from the competitive immunoassay of Example 4.

Example 4 with Reference to FIGS. 3 and 11:
Mn-Doped ZnS Nanoparticle-Labeled
Electroluminescent Competitive Immunoassay for
Anti-BSA Antibody A. Conjugating BSA on the IDE-NH$_2$ The preparation of BSA conjugated electrodes (IDE-BSA) is described herein. 500 µL of DI water, 8 µL of BSA (1 mg/mL solution in PBS) 302, 12 µL of EDC (3 µg/mL in DI water) and 3 µL of NHS (26 µg/mL in DI water) were added to a reaction tube to make solution B. Solution B was incubated for 15 minutes at room temperature. After 15 minutes, 30 µL of solution B was spread on the IDE-NH$_2$. The electrodes 301 were incubated on an orbital shaker at room temperature for 2 hours. After 2 hours the electrodes were washed 3 times with wash buffer and rinsed with PBS.

B. Blocking the Non-Specific Binding Sites

20 µL of blocking buffer was added to each IDE-BSA. The electrodes were placed on an orbital shaker and incubated at room temperature for 1 hour. After the incubation, the electrodes were washed 3 times with wash buffer and rinsed with PBS.

C. Adding the sample 5 µL of anti-BSA (2 mg/mL) 303 was added to 200 µL of PBS and labeled as the first analyte solution. Second analyte solution to fifth analyte solution were prepared by serial dilution of the first analyte solution in PBS. A 200 µL PBS solution was labeled as PBS solution.

A NPs-Ab solution 304-305 was prepared as described in previous examples. A 600 µL portion of NPs-Ab was mixed with 400 µL PBS and labeled as competitive reagent solution. Blank solution was prepared by mixing 100 µL of PBS solution with 100 µL of competitive reagent solution. First sample solution to fifth sample solution were prepared by adding 100 µL of competitive reagent to 100 µL of first analyte solution to fifth analyte solution, respectively. Blank sample was prepared by adding 20 µL of the blank solution to a blocked IDE-BSA. First to fifth samples were prepared by adding 20 µL of the first to fifth sample solutions to blocked IDE-BSA, respectively. The electrodes were incubated at room temperature on an orbital shaker for 1 hour. After the incubation, the electrodes (IDE-BSA-Ab-NPs) were washed 3 times with wash buffer and rinsed with PBS and DI water. The IDE-BSA-Ab-NPs then were dried.

D. Imaging.

The imaging procedure was described in example 3-E. Digital images of each of the serial dilutions of analyte processed in accordance with the above protocol are shown in FIG. 11.

Figure 4:
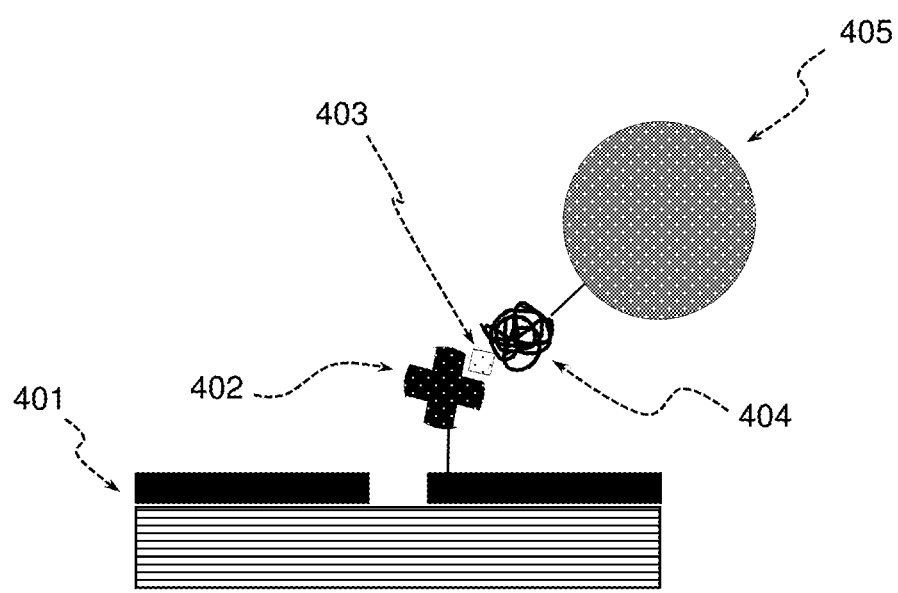
FIG. 4 is a diagram depicting an example embodiment of an electroluminescent binding assay for biotin as described in Example 5.
Figure 12:
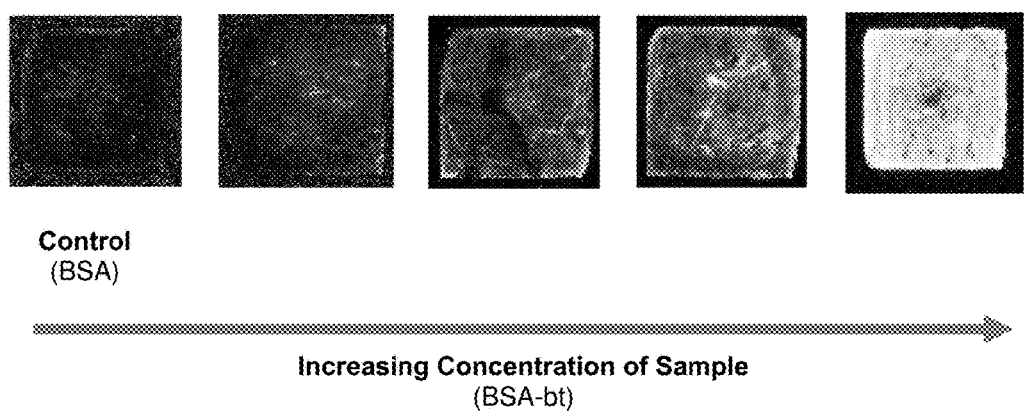
FIG. 12 depicts images from the binding assay for biotin of Example 5.

Example 5 with Reference to FIGS. 4 and 12:
Cu-Doped ZnS Nanoparticle-Labeled
Electroluminescent Binding Assay for Biotin A. Conjugating Streptavidin on the IDE-NH$_2$.

Preparation of Streptavidin (StA) conjugated electrodes (IDE-StA) is described herein. 500 µL of DI water, 8 µL of StA 402 (1 mg/mL solution in DI water), 48 µL of EDC (3 µg/mL in DI water) and 12 µL of NHS (26 µg/mL in DI water) were added to a reaction tube to make solution C. Solution C was incubated for 15 minutes at room temperature. After 15 minutes, 30 µL of solution C was spread on the IDE-NH$_2$. The electrodes 401 were incubated on an orbital shaker at room temperature for 2 hours. After 2 hours the electrodes were washed 3 times with wash buffer and rinsed with PBS.

B. Blocking the Non-Specific Binding Sites.

The non-specific binding sites on the IDE-StAs were blocked with the same procedure described in previous examples.

C. Labeling the Biotinylated—BSA with Cu Doped ZnS Nanoparticles.

A preparation method for the passive conjugation of Biotinylated BSA (hereafter called bt-BSA) to the 0.2% Cu-doped ZnS nanoparticles (20 nm average diameter) (NPs-BSA-bt) is described herein. 60 µl of Cu doped ZnS nanoparticles (10 mg/mL in DI water) were suspended in deionized (DI) water (1 ml) to form a suspension. The suspension was divided into five different centrifuge tubes, labeled as tube 1 to tube 5. 38 µL of bt-BSA (2 mg/mL in PBS) 403-404 was diluted in 200 µL of PBS to make stock sample solution. The samples were prepared by adding 100 µL of the serial dilution of the stock sample solutions in tubes 1 to 4. In another tube, 38 µL of BSA (2 µg/mL) was added to 200 µL of PBS to make the control solution. The control sample was prepared by adding 100 µL of the control solution to tube 5. The tubes were incubated for 2 hours at room temperature. The suspension was centrifuged at 14000 RPM for 10 minutes and the supernatant was decanted. For the purification step, the precipitates were re-dispersed in PBS and centrifuged again at 14000 RPM for 10 minutes and the supernatant was decanted. The purification step was repeated for 3 times. After the last purification step, the precipitates were dispersed in 1 mL of PBS.

D. Adding the Samples to IDE-StA.

20 µL of NPs-BSA-bt was added to the IDE-StA and was incubated at room temperature on an orbital shaker for 1 hour. The control sample was prepared by adding 20 µL of NPs-BSA to the IDE-StA and was incubated at room temperature on an orbital shaker for 1 hour. After the incubation, the sample and the control electrodes were washed 3 times with wash buffer and rinsed with PBS and DI water.

E. Imaging.

The imaging procedure was described in example 3-E. Digital images of each of the serial dilutions of analyte processed in accordance with the above protocol are shown in FIG. 12.

Figure 5:
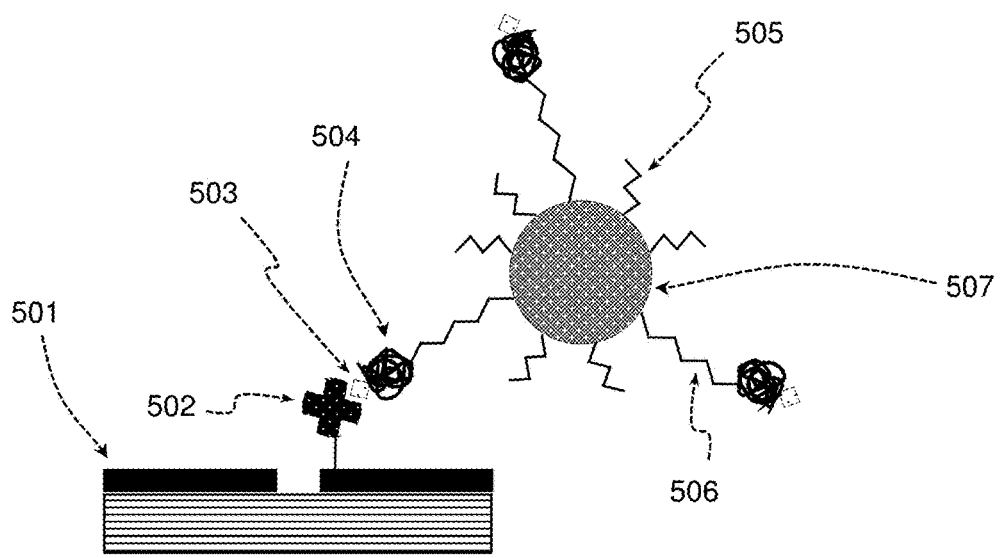
FIG. 5 is a diagram depicting an example embodiment of an electroluminescent binding assay for biotin using nanoparticles coated with PEG linkers as described in Example 6.
Figure 13:
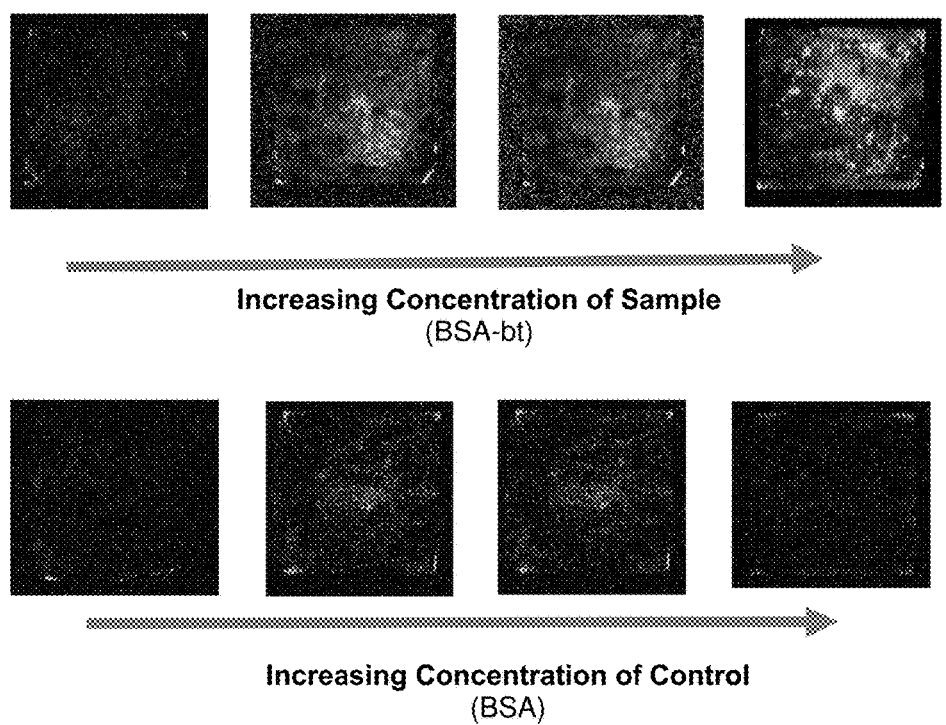
FIG. 13 depicts images from the binding assay for biotin of Example 6.

Example 6 with Reference to FIGS. 5 and 13:
Poly(Ethylene)Glycol (PEG) Modified Mn-Doped
ZnS Nanoparticles Labeled Electroluminescent
Binding Assay for Biotin A. Conjugating Streptavidin on the IDE-NH$_2$.

StA conjugated IDEs (IDE-StAs) 501-502 were prepared as described in example 5-A.

B. Blocking the Non-Specific Binding Sites.

The non-specific binding sites on the IDE-StAs were blocked with the same procedure described in previous examples.

C. Preparation of PEG-Modified NPs.

For the preparation of PEG-modified NPs (NPs-PEG), 30 µL of MPA-capped Mn doped ZnS nanoparticles 507 (50 nm particle size, 10 mg/mL) were suspended in DI water (1 mL) to form a suspension. 2.1 µL of EDC (3 mg/mL in DI water) was added to the suspension and the suspension was mixed for 1 minute at room temperature. After 1 minute, 5 µL of NHS (2.6 mg/mL in DI water) was added to the suspension. The suspension was incubated for 15 minutes at room temperature. 6 µL of 2ME (1:1000 V/V solution in DI water) was added to the suspension to make a reaction mixture. 100 µL of Amine PEG Acetic Acid 506 (hPEG, JenKem Technology, 10 mg/mL) and 120 µL of Methoxy PEG Amine 505 (mPEG, JenKem Technology, 10 mg/mL) were added to the reaction mixture and the reaction mixture was incubated for 2 hours at room temperature. Reaction mixture was centrifuged at 14000 RPM for 10 minutes and the supernatant was decanted. For the purification step, the precipitates were redispersed in DI water and centrifuged again at 14000 RPM for 10 minutes and the supernatant was decanted. The purification step was repeated for 3 times. After the last purification step, the precipitates were dispersed in 1 mL of DI water.

D. Labeling the Biotinylated BSA with PEG-Modified NPs (NPs-PEG-BSA-bt)

21 µL of EDC (30 µg/mL in DI water) was added to 1 mL of the NPs-PEG suspension prepared as described in example 6-B. The suspension was mixed for 1 minute at room temperature. After 1 minute, 5 µL of NHS (260 µg/mL in DI water) was added to the suspension and the suspension was incubated for 15 minutes at room temperature. 2 µL of 2ME (1:1000 V/V solution in DI water) was added to the suspension. The suspension was divided into five microcentrifuge tubes and labeled as tube 1 to tube 5. A first bt-BSA 503-504 solution was prepared at the concentration of 1.5 mg/mL in PBS. A second to a fourth bt-BSA solutions were prepared by serial dilution of the first bt-BSA (1/10 V/V in PBS). A first to a fourth sample were prepared by adding 5 µL of the first bt-BSA solution to the fourth bt-BSA solution to the tube 1 to tube 4, respectively. The blank was prepared by adding 5 µL of PBS to the tube 5. All tubes were incubated at room temperature for 2 hours, and then centrifuged at 14000 RPM for 10 minutes. The supernatants were decanted. For the purification step, the precipitates were redispersed in PBS and centrifuged again at 14000 RPM for 10 minutes and the supernatant was decanted. The purification step was repeated for 3 times. After the last purification step, the precipitates were dispersed in 200 µL of PBS.

E. Labeling BSA with PEG-Modified NPs (NPs-PEG-BSA) as Controls

The control samples were prepared by the same procedure described in example VI-C, replacing the bt-BSA with BSA F. Adding the Samples to IDE-StA Samples, controls, and blank electrodes were prepared by adding 20 µL of sample 1 to sample 4, control 1 to control 4 and blanks to different IDE-StAs and the electrodes were incubated at room temperature on an orbital shaker for 1 hour. After the incubation, electrodes were washed 3 times with wash buffer and rinsed with PBS and DI water.

G. Imaging.

The imaging procedure was described in example 3-E. Digital images of each of the serial dilutions of analyte and controls processed in accordance with the above protocol are shown in FIG. 13.

Figure 6:
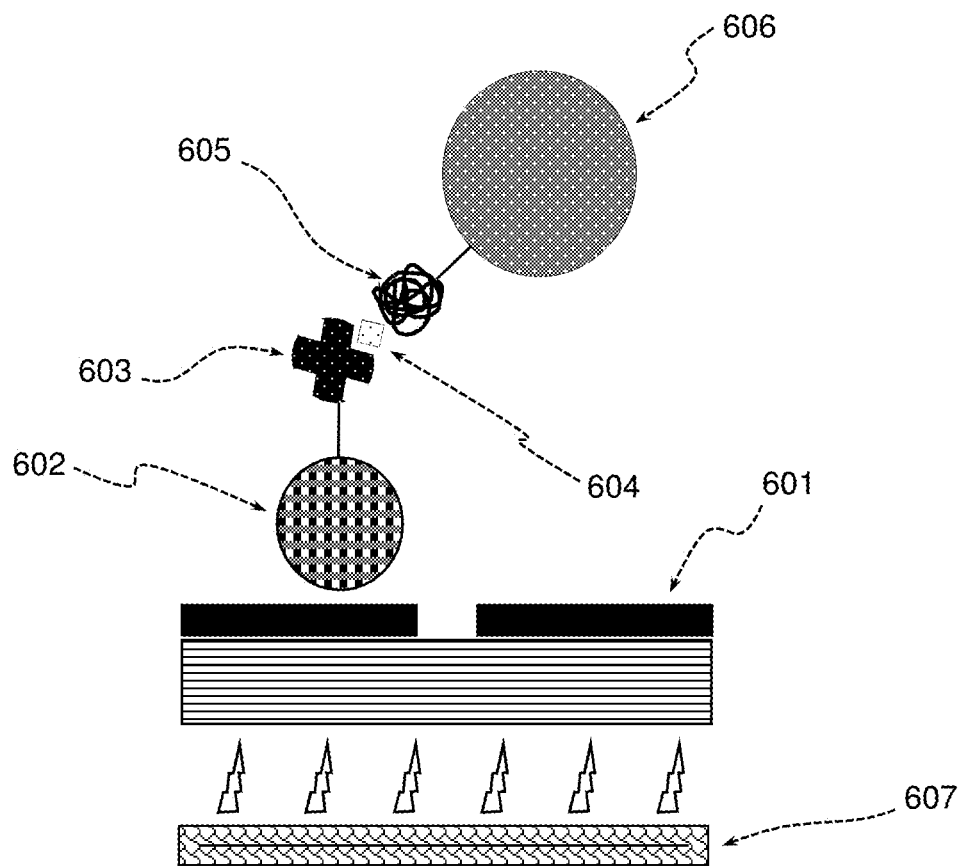
FIG. 6 is a diagram depicting an example embodiment of an electroluminescent binding assay for biotin as described in Example 7 where a streptavidin conjugated magnetic capture particle is drawn to the electrodes with an external magnet.
Figure 14:
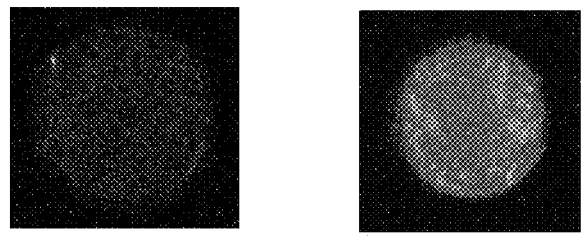
FIG. 14 depicts images from the magnetic capture particle assay for biotin of Example 7.

Example 7 with Reference to FIGS. 6 and 14:
Cu-Doped ZnS Nanoparticles Labeled Magnetic
Beads-Base Electroluminescent Assay for Biotin A. Labeling Bt-BSA with Cu Doped NPs (NPs-BSA-Bt)

NPs-BSA-bt (i.e. 606-605-604 conjugates) were prepared with the same procedure as described in example 5-B.

B. Preparation of Samples

25 µL of streptavidin conjugated magnetic beads 603-602 (MB-StA—Pierce Streptavidin Magnetic Beads, Thermo Scientific, 10 mg/mL) was dispersed in 1 mL of DI water. The suspension was washed by isolating the magnetic beads from the solution using a magnetic bead separation stand and withdrawing the solution. After repeating the washing step for 3 times, the MB-StA was dispersed in 1 mL of blocking buffer and incubated for 1 hour. The washing step was repeated after the incubation and the MB-StA was dispersed in DI water after washing. The analyte suspension was prepared by mixing 100 µL of MB-StA suspension with 50 µL of NPs-BSA-bt prepared in the previous step. The control suspension was prepared by mixing 100 µL of MB-StA with 50 µL of NPs-BSA. Analyte sample and control sample were incubated for 2 hours, following by 3 times washing with PBS as described before. After washing, 20 µL of analyte and control suspension on different clean IDEs 601. The IDEs were placed over a magnet 607 to bring the MB-StA-bt-BSA-NPs to the surface of the electrode.

C. Imaging

The imaging procedure was described in example 3-E, without adding additional DI water on the IDEs. Digital images of each of the serial dilutions of analyte processed in accordance with the above protocol are shown in FIG. 14.

Figure 7:
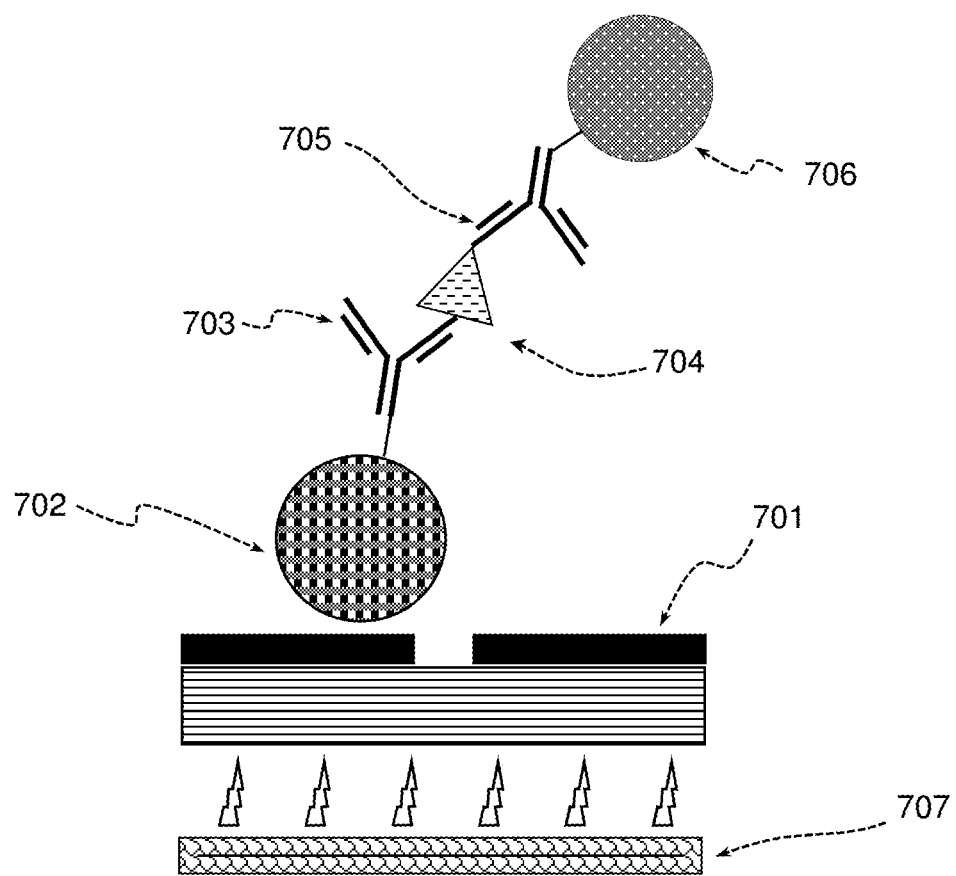
FIG. 7 is a diagram depicting an example embodiment of an electroluminescent sandwich immunoassay as described in Example 8 where an antibody conjugated to a magnetic capture particle is drawn to the electrodes with an external magnet.
Figure 15:
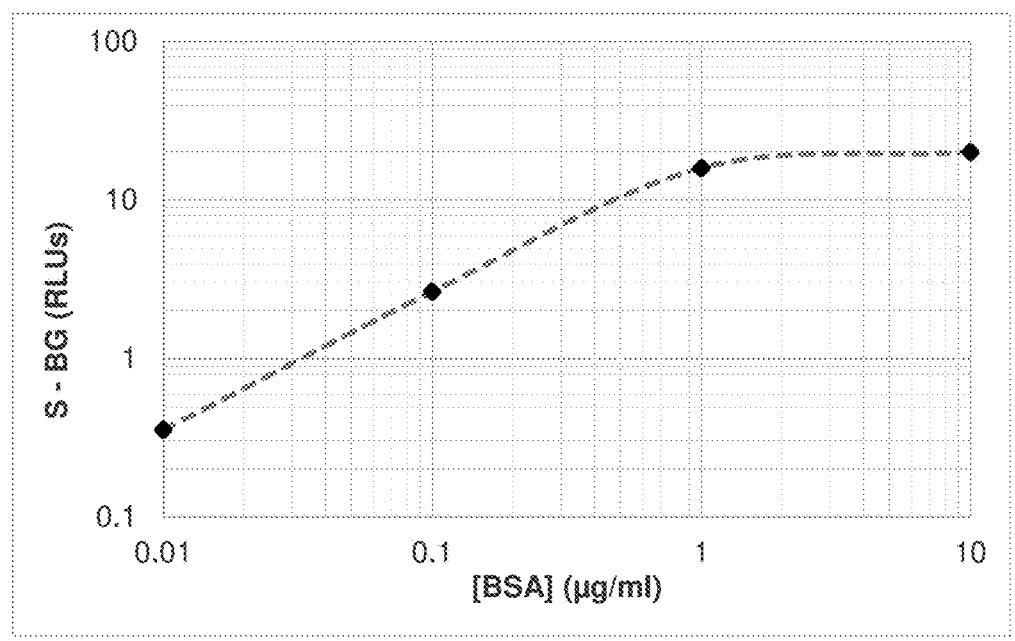
FIG. 15 is a plot depicting the sandwich immunoassay format of Example 8.

Example 8 with Reference to FIGS. 7 and 15:
Mn-Doped ZnS Nanoparticles Labeled Magnetic
Beads-Base Sandwich Electroluminescent
Immunoassay for BSA A. Preparation of Electroluminescent Nanoparticles-Labeled Antibody The NPs-Ab 706-705 were prepared as described in example 2.

B. Preparation of Biotinylated Capture Antibody

In a centrifuge tube, 30 μL of mAnti-BSA 703 (200 mg/mL) was added to 500 μL of PBS. 2 μL of sulfo-NHS biotinylation kit was added to the solution in the tube, and the mixture was incubated on an orbital shaker over ice for 2 hours. After the incubation, the mixture was passed through a desalting column and mAnti-BSA-bt was collected.

C. Preparation of Samples

10 μL of MB-StA 702 (10 mg/mL) was added to the 500 μL of mAnti-BSA-bt and the mixture was incubated on a rocker for 1 hour. After the incubation, the suspension was washed by isolating the magnetic beads from the solution using a magnetic bead separation stand and withdrawing the solution. The washing step was repeated once with wash buffer and two times with PBS. After the last washing step, the MB-StA-bt-mAnti-BSA was dispersed in 500 μL of the blocking buffer. The suspension was incubated for 1 hour and after the incubation the washing steps were repeated. After the washing steps the blocked MB-StA-bt-mAnti-BSA was dispersed in 500 μL of PBS.

A serial dilution of BSA 704 in PBS was prepared with the range of concentration of BSA varying from 10 μg/mL to 10 ng/mL, and 100 μL of these solutions were added to four different tubes, labeled as tube 1 to tube 4, respectively. A blank sample was prepared in a fifth tube, by adding 100 μL of PBS. Then 100 μL of MB-StA-bt-mAnti-BSA was added to tube 1 to tube 5. The mixture was incubated for 1 hour at room temperature and after incubation, the washing steps were repeated.

After the last washing step, 100 μL of the NPs-AB was added to the tubes and incubated for 1 hour on an orbital shaker at room temperature for 1 hour. The washing steps were repeated after the incubation time with two extra washing steps with DI water. After the washing steps, 50 μL of DI water was added to each tube and the samples were imaged.

D. Imaging

An IDE 701 was rinsed with ethanol, dried, secured on a holder and placed inside a dark box with a built-in camera on top of the dark box. 15 μL of the suspension from tube 1 was placed over the IDE and a magnet 707 was placed under the IDE so that the magnetic beads come to the proximity of the surface of the IDE. A time varying voltage having a square wave profile with a frequency of 57 Hz and peak-to-peak amplitude of 60 V was applied to the IDEs. A CCD camera was used for imaging the electroluminescence signal.

Digital images of each of the serial dilutions of analyte processed in accordance with the above protocol are shown in FIG. 15.

Figure 8:
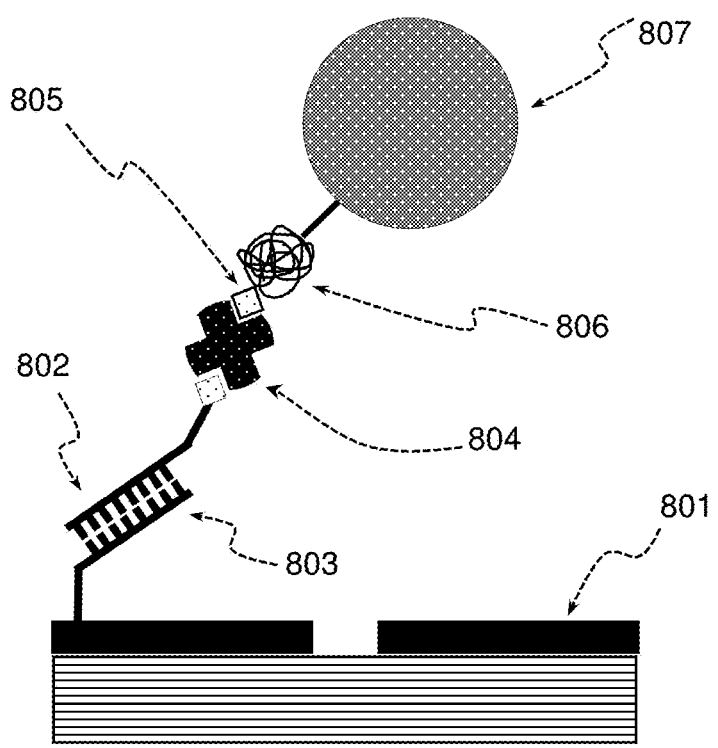
FIG. 8 is a diagram depicting an example embodiment of a nucleic acid hybridization assay as described in Example 9.
Figure 16:
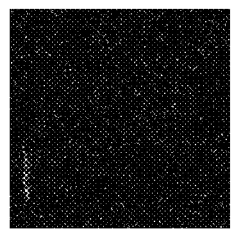
FIG. 16 depicts images from the nucleic acid hybridization assay of Example 9.
Figure 16:
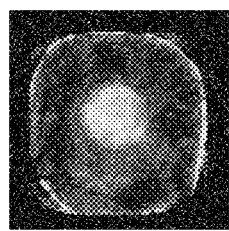

Example 9 with Reference to FIGS. 8 and 16:
Mn-Doped ZnS Nanoparticle Electroluminescent Hybridization Assay for DNA A. Preparation of Amine-Functionalized Primary Oligonucleotide The process for amine-functionalization of the 5'-phosphate end of the primary oligonucleotide 802 is described herein. First a reaction buffer was prepared by adding 3 mg of ethylenediaminetetraacetic acid (EDTA, 99.995%, Sigma-Aldrich) and 87 mg of sodium chloride (NaCl, >99.0%, Sigma-Aldrich) to 10 mL of PBS (10 mM). A solution A was prepared by adding 10 nmol of primary oligonucleotide (50 bases single-stranded DNA, Sigma Life Science) to 10 μL of the reaction buffer. A solution B was prepared by mixing 1.7 μL ethylenediamine (analytical standard, Sigma-Aldrich) with 100 μL of Imidazole solution (>99%, Sigma-Aldrich, 0.1 M in DI water). In a centrifuge tube, 1.2 mg of EDC was added. Then 7.5 μL of solution A was added to the tube, and immediately 5 μL of solution B was added to the mixture. The mixture was vortex'd for 1 minute and then 20 μL of imidazole solution (0.1 M in DI water) was added to the mixture. The mixture was incubated at room temperature overnight. After the incubation, the mixture was desalted using a column (Zeba Spring Desalting Column 7K MWCO, Thermo Scientific). The desalted mixture was labeled as pOligo-NH$_2$.

B. Biotinylation of pOligo-NH$_2$

To prepare the biotinylated primary oligonucleotide (pOligo-bt), 100 μL of pOligo-NH$_2$ (10 nm in 100 μL of reaction buffer) was added to 250 μL of PBS. 60 μL of sulfo-NHS-biotin (EZ-Link Micro Sulfo-NHS-SS-Biotinylation Kit, ThermoFisher Scientific) was added to the mixture and the mixture was incubated on an orbital shaker over ice for 2 hours. After the incubation, the mixture was passed through a desalting column and pOligo-bt was collected.

C. Conjugating the Complementary Oligonucleotide on the IDEs

Amine-functionalized complementary oligonucleotide 803 (cOligo-NH$_2$) was prepared using the method described in example 8-A. Activated electrodes (IDE-NH$_2$) 801 were washed three times with PBS and dried. 30 μL of glutaraldehyde solution (Sigma-Aldrich, 10% solution in DI water) was incubated over the IDE-NH$_2$ for 1 hour. Then the IDEs were washed 5 times with PBS and dried. Then 30 μL of the cOligo-NH$_2$ solution (100 pmol in 30 μL of PBS) was added to the IDEs and the IDEs were incubated at room temperature on an orbital shaker for 2 hours. After the incubation the reaction was quenched by adding 10 μL of Tris base solution (Fisher Bioreagents, 6% solution in DI water). 5 μL of sodium cyanoborohydride solution (95%, Sigma-Aldrich, 10 mM solution in DI water) was added to the mixture over the IDEs and was incubated at room temperature for 15 minutes. After incubation, the IDE-cOligo were washed with PBS.

D. Pre-Hybridization Procedure

A solution D was prepared by mixing 100 μL of sodium chloride solution (>99%, Sigma-Aldrich, 0.15 M solution in DI water) and 100 μL of sodium citrate solution (>99.0%, Sigma-Aldrich, 0.015M solution in DI water). A pre-hybridization blocking solution was prepared by mixing 140 μL of solution D, 360 μL of Denhardt's solution (Sigma-Aldrich, 1× solution in DI water) containing 100 μg of denatured salmon sperm DNA (deoxyribonucleic acid sodium salt from salmon testes, Sigma Life Science), and 500 μL of formamide (>99.5%, Sigma-Aldrich). 30 μL of the pre-hybridization blocking solution was incubated over the IDE-cOligos for 30 minutes at 50° C. After incubation, the IDEs were washed with a prehybridization wash buffer, comprise of the reaction buffer and 0.5% sodium dodecylsulfate (>99%, Research Products International Corp.) and rinsed with the reaction buffer.

E. Hybridization Procedure

A hybridization buffer was prepared by adding 1 μg of pOligo-bt in 1 mL of reaction buffer, containing 2.5% Dextran (Dextran sulfate sodium salt from *Leuconostoc* spp., Sigma-Aldrich). 30 μL of the hybridization buffer was incubated over the IDE-cOligos for 30 minutes at 50° C. After the incubation the IDEs (IDE-cOligo-pOligo-bt) were washed with the hybridization wash buffer. Control sample was prepared by following procedures 9A to 9E, with replacing the cOligo with another 50 bases single-stranded DNA which was not complementary to the pOligo.

F. Adding Streptavidin to the IDE-cOligo-pOligo-bts

On the IDE-cOligo-pOligo-bts, 30 μL of streptavidin 804 (12 μg/mL in PBS) was added and the IDEs were incubated at room temperature on an orbital shaker for 1 hour. After the incubation, the IDE-cOligo-pOligo-bt-StAs were washed with wash buffer (0.05% Tween 20 in PBS) and rinsed with PBS.

G. Adding Mn-doped ZnS Nanoparticles labeled Biotinylated BSA NPs-BSA-bt (i.e. 807-806-805 conjugate) were prepared as described in example 5-B. 20 μL of the NPs-BSA-bt was added to the IDE-cOligo-pOligo-bt-StAs and the IDEs were incubated at room temperature on an orbital shaker for 1 hour. After the incubation, the IDEs were washed with wash buffer and rinsed with PBS.

H. Imaging

The imaging procedure was described in example 3-E. Digital images of each of the serial dilutions of analyte processed in accordance with the above protocol are shown in FIG. 16.

Figure 9:
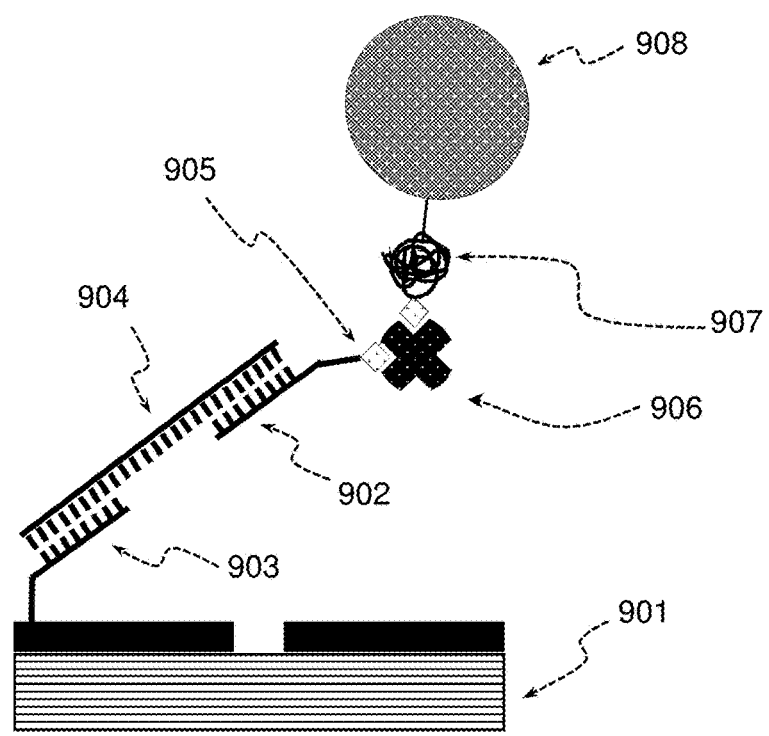
FIG. 9 is a diagram depicting an example embodiment of a nucleic acid sandwich hybridization assay as described in Example 10.
Figure 17:
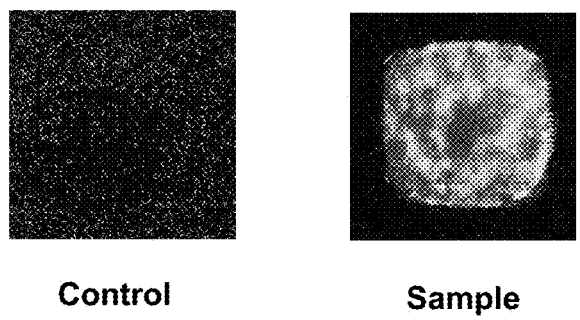
FIG. 17 depicts images from the nucleic acid sandwich hybridization assay of Example 10.

Example 10 with Reference to FIGS. 9 and 17:
Mn-Doped ZnS Nanoparticle Electroluminescent Sandwich Hybridization Assay for DNA A. Biotinylation of Primary Oligonucleotide (pOligo-Bt)

The procedure for biotinylation of pOligo 905-902 was described in example 9-B.

B. Conjugation of the Complementary Oligonucleotide on the IDEs (IDE-cOligo)

The procedure for conjugating the cOligo 903 on IDE was described in example 9-C.

C. Pre-Hybridization Process

The pre-hybridization process and blocking the IDE-cOligos were performed as described in example 9-D.

D. Hybridization Process

A hybridization buffer was prepared by adding 10 μL of pOligo-bt (100 μM) and 10 μL of analyte oligonucleotide 904 (aOligo, 120 bases single-stranded DNA, Sigma Life Science) in 300 μL of reaction buffer, containing 2.5% Dextran (Dextran sulfate sodium salt from *Leuconostoc* spp., Sigma-Aldrich). 30 μL of the hybridization buffer was incubated over the IDE-cOligos for 30 minutes at 55° C. After the incubation the IDEs (IDE-cOligo-aOligo-pOligo-bt) were washed with the hybridization wash buffer. The control sample was prepared with the same procedure, without addition of the aOligo.

Streptavidin 906 addition and NPs-labeled biotinylated BSA (908-907-906) addition steps were performed as described in examples 9-F and 9-G.

E. Imaging

The imaging procedure was described in example 3-E. Digital images of each of the serial dilutions of analyte processed in accordance with the above protocol are shown in FIG. 17.

What is claimed is:

1. A method for detecting a target species in a sample suspected of containing the target species by producing electroluminescence in a liquid medium comprising:
providing a solid support having disposed thereon at least one pair of electrodes to which is immobilized a first specific binding partner which is capable of binding to the target species;
providing an electroluminescent nanoparticle label as a conjugate, wherein the nanoparticle is bound to either an analog of the target species or to a second specific binding partner of the target species;
combining the sample and the electroluminescent nanoparticle conjugate in an aqueous solution to form a mixture;
applying the mixture to the solid support to specifically bind the target species to the first specific binding partner and thereby bring the electroluminescent nanoparticle conjugate into operable proximity to the electrodes;
removing materials not bound to the solid support;
adding a liquid medium;
applying a time-varying excitation signal between the electrodes in the pair of electrodes with an excitation source electrically coupled to the pair of electrodes, thereby exciting the nanoparticles to produce electroluminescence; and
detecting the electroluminescence produced while the electrical excitation is being applied, wherein the electroluminescence indicates the presence of the target species in the sample.

2. The method of claim 1 wherein the nanoparticles are comprised of one or more of a metal chalcogenide, a group IIB-VI semiconductor compound or a group III-V semiconductor compound.

3. The method of claim 1 wherein the nanoparticles are comprised of a material selected from the group consisting of ZnO, ZnS, ZnSe, CdS, CdSe, CdTe, GaAs, PbS and composite nanoparticles having a CdSe core with ZnS shell.

4. The method of claim 3 wherein the nanoparticles are doped with a dopant selected from the group consisting of transition metals and rare earth metals.

5. The method of claim 1 wherein the liquid medium is polar.

6. The method of claim 1 wherein the liquid media is selected from a group consisting of water, dimethyl sulfoxide, and dimethylformamide.

7. The method of claim 1 wherein the liquid medium is an aqueous buffer solution further includes electrolytes.

8. The method of claim 1 wherein the electrodes in the pair of electrodes are interdigitated.

9. The method of claim 1 wherein the electrodes are comprised of aluminum or aluminum alloys.

10. The method of claim 1 wherein the electrodes are comprised of gold or platinum.

11. The method of claim 1 wherein the excitation source applies a voltage between the electrodes in the pair of electrodes, where the voltage periodically changes from a first value to a second value and vice versa.

12. The method of claim 11 wherein the excitation is in the form of pulses of voltage applied between the electrodes and wherein the pulses are separated by a period of time in which the magnitude of the voltage is a baseline value that is less than peak value of the pulses.

13. The method of claim 11 wherein the voltage applied between the electrodes alternates from positive to negative.

14. The method of claim 1 used in a specific binding assay selected from the group consisting of an immunoassay, a nucleic acid hybridization assay, a receptor binding assay, an immunocytochemical assay and an immunohistochemical assay.

15. The method of claim 14 wherein the immunoassay is selected from a sandwich immunoassay and a competitive immunoassay.

16. The method of claim 14 wherein the first specific binding partner is an antibody capable of specifically binding to the target species and wherein the target species is an antigen.

17. The method of claim 14 wherein the first specific binding partner is an antigen and wherein the target species is an antibody capable of specifically binding to the target species.

18. The method of claim 14 wherein the first specific binding partner is a binding protein selected from streptavidin and antibodies and wherein a hapten bindable to the binding protein is provided as a label on the target species.

19. The method of claim 18 wherein the hapten is selected from the group consisting of biotin, digoxigenin, fluorescein and dinitrophenol.

20. The method of claim 1 wherein the target species is a protein that is passively adsorbed or chemically conjugated to the electroluminescent nanoparticle.

21. The method of claim 1 wherein the target species is a nucleic acid and the first specific binding partner is a nucleic acid having a sequence region that is substantially complementary to a first region of the target species nucleic acid.

22. The method of claim 21 further comprising hybridizing a second nucleic acid bound to the electroluminescent nanoparticle to a second region of the target species nucleic acid.

23. The method of claim 1 further comprising measuring the intensity of the electroluminescence produced and relating the intensity to the amount of the target species.

24. A method for detecting a target species in a sample suspected of containing the target species by producing electroluminescence in a liquid medium comprising:
providing a solid support having disposed thereon at least one pair of electrodes;
providing a capture particle conjugate comprising a nanoparticle bound to a first specific binding partner of the target species;
providing an electroluminescent nanoparticle label as a conjugate, wherein the electroluminescent nanoparticle is bound to either an analog of the target species or to a second specific binding partner of the target species;
combining the sample, the capture particle conjugate, and the electroluminescent nanoparticle conjugate in a liquid medium to form a mixture for a time sufficient for specific binding to occur, thereby associating the electroluminescent nanoparticle with the capture particle;
immobilizing the capture particle conjugates onto the solid support to thereby bring the electroluminescent nanoparticle conjugate into operable proximity to the electrodes;
removing materials not bound to the capture particle;
applying a time-varying excitation signal between the electrodes in the pair of electrodes in the presence of added liquid medium with an excitation source electrically coupled to the pair of electrodes, thereby exciting the nanoparticles to produce electroluminescence; and
detecting the electroluminescence produced while the electrical excitation is being applied, wherein the presence of electroluminescence indicates the presence of the target species in the sample.

25. The method of claim 24 wherein the capture particle is magnetically responsive and is immobilized on the electrodes.

26. The method of claim 24 wherein the capture particle is magnetically responsive and is immobilized on the electrodes with a magnetic field.

27. The method of claim 24 wherein the nanoparticles are comprised of one or more of a metal chalcogenide, a group IIB-VI semiconductor compound or a group III-V semiconductor compound.

28. The method of claim 24 wherein the nanoparticles are comprised of a material selected from the group consisting of ZnO, ZnS, ZnSe, CdS, CdSe, CdTe, GaAs, PbS and composite nanoparticles having a CdSe core with ZnS shell.

29. The method of claim 28 wherein the nanoparticles are doped with a dopant selected from the group consisting of transition metals and rare earth metals.

30. The method of claim 24 wherein the liquid medium is polar.

31. The method of claim 24 wherein the liquid media is selected from a group consisting of water, dimethyl sulfoxide, and dimethylformamide.

32. The method of claim 24 wherein the liquid medium is an aqueous buffer solution further includes electrolytes.

33. The method of claim 24 wherein the electrodes in the pair of electrodes are interdigitated.

34. The method of claim 24 wherein the electrodes are comprised of aluminum or aluminum alloys.

35. The method of claim 24 wherein the electrodes are comprised of gold or platinum.

36. The method of claim 24 wherein the excitation source applies a voltage between the electrodes in the pair of electrodes, where the voltage periodically changes from a first value to a second value and vice versa.

37. The method of claim 36 wherein the excitation is in the form of pulses of voltage applied between the electrodes and wherein the pulses are separated by a period of time in which the magnitude of the voltage is a baseline value that is less than peak value of the pulses.

38. The method of claim 36 wherein the voltage applied between the electrodes alternates from positive to negative.

39. The method of claim 24 used in a specific binding assay selected from the group consisting of an immunoassay, a nucleic acid hybridization assay, a receptor binding assay, an immunocytochemical assay and an immunohistochemical assay.

40. The method of claim 39 wherein the immunoassay is selected from a sandwich immunoassay and a competitive immunoassay.

41. The method of claim 39 wherein the first specific binding partner is an antibody capable of specifically binding to the target species and wherein the target species is an antigen.

42. The method of claim 39 wherein the first specific binding partner is an antigen and wherein the target species is an antibody capable of specifically binding to the target species.

43. The method of claim 39 wherein the first specific binding partner is a binding protein selected from streptavidin and antibodies and wherein a hapten bindable to the binding protein is provided as a label on the target species.

44. The method of claim 43 wherein the hapten is selected from the group consisting of biotin, digoxigenin, fluorescein and dinitrophenol.

45. The method of claim 24 wherein the target species is a protein that is passively adsorbed or chemically conjugated to the electroluminescent nanoparticle.

46. The method of claim 24 wherein the target species is a nucleic acid and the first specific binding partner is a nucleic acid having a sequence region that is substantially complementary to a first region of the target species nucleic acid.

47. The method of claim 46 further comprising hybridizing a second nucleic acid bound to the electroluminescent nanoparticle to a second region of the target species nucleic acid.

48. The method of claim 24 further comprising measuring the intensity of the electroluminescence produced and relating the intensity to the amount of the target species.

49. The method of claim 1 wherein the step of removing materials not bound to the solid support is performed by washing the support with a wash solution.

50. The method of claim 24 wherein the step of removing materials not bound to the capture particle is performed by washing the capture particle with a wash solution.

51. The method of claim 24 wherein the step of removing materials not bound to the capture particle is performed before immobilizing the capture particle conjugates onto the solid support.

52. The method of claim 24 wherein the step of removing materials not bound to the capture particle is performed before immobilizing the capture particle conjugates onto the solid support.

\* \* \* \* \*

UNITED STATES PATENT AND TRADEMARK OFFICE
CERTIFICATE OF CORRECTION

PATENT NO. : 10,241,111 B2
APPLICATION NO. : 16/119036
DATED : March 26, 2019
INVENTOR(S) : Hashem Akhavan-Tafti et al.

It is certified that error appears in the above-identified patent and that said Letters Patent is hereby corrected as shown below:

In the Specification

Column 1, Line 48, please delete "U.S. Ser. No. 10/021,761B2" and insert --U.S. Pat. No. 10,021,761B2-- therefor.

Column 15, Line 33, please delete "ImageJ" and insert --Image-- therefor.

Column 22, Line 54, please delete "50° C" and insert --50 °C-- therefor.

Column 22, Line 64, please delete "50° C" and insert --50 °C-- therefor.

Column 23, Line 44, please delete "55° C" and insert --55 °C-- therefor.

Column 23, Line 48, after "addition of" please delete "¶".

Signed and Sealed this
Second Day of July, 2019

Andrei Iancu
*Director of the United States Patent and Trademark Office*